US009186375B2

(12) United States Patent
Marcum et al.

(10) Patent No.: US 9,186,375 B2
(45) Date of Patent: Nov. 17, 2015

(54) GLYCOSAMINOGLYCAN COMPOSITIONS IN COMBINATION WITH STEM CELLS

(75) Inventors: Frank D. Marcum, Lexington, KY (US); James Conway, Clermont, FL (US)

(73) Assignee: ARTHRODYNAMIC TECHNOLOGIES, ANIMAL HEALTH DIVISION, INC., Lexington, KY (US)

( * ) Notice: Subject to any disclaimer, the term of this patent is extended or adjusted under 35 U.S.C. 154(b) by 270 days.

(21) Appl. No.: 13/545,327

(22) Filed: Jul. 10, 2012

(65) Prior Publication Data

US 2012/0276173 A1 Nov. 1, 2012

Related U.S. Application Data

(63) Continuation-in-part of application No. 11/766,510, filed on Jun. 21, 2007, now Pat. No. 8,455,458.

(51) Int. Cl.

| A61K 35/12 | (2015.01) |
|---|---|
| A61K 31/737 | (2006.01) |
| A61K 31/715 | (2006.01) |
| A61K 45/06 | (2006.01) |
| A61K 31/728 | (2006.01) |
| A61K 31/726 | (2006.01) |
| A61K 38/18 | (2006.01) |
| A61L 27/26 | (2006.01) |
| A61K 35/28 | (2015.01) |
| A61K 35/35 | (2015.01) |
| A61L 27/34 | (2006.01) |
| A61L 27/38 | (2006.01) |
| A61L 27/54 | (2006.01) |
| A61K 38/27 | (2006.01) |
| A61K 38/30 | (2006.01) |
| A61B 17/06 | (2006.01) |
| A61B 17/064 | (2006.01) |
| A61B 17/00 | (2006.01) |

(52) U.S. Cl.
CPC ............... *A61K 31/715* (2013.01); *A61K 35/28* (2013.01); *A61K 35/35* (2013.01); *A61K 38/18* (2013.01); *A61K 38/1825* (2013.01); *A61K 38/1841* (2013.01); *A61K 38/1875* (2013.01); *A61K 38/27* (2013.01); *A61K 38/30* (2013.01); *A61K 45/06* (2013.01); *A61L 27/26* (2013.01); *A61L 27/34* (2013.01); *A61L 27/3834* (2013.01); *A61L 27/3852* (2013.01); *A61L 27/54* (2013.01); *A61B 17/064* (2013.01); *A61B 17/06166* (2013.01); *A61B 2017/00004* (2013.01); *A61L 2300/41* (2013.01); *A61L 2300/414* (2013.01); *A61L 2300/426* (2013.01); *A61L 2300/43* (2013.01); *A61L 2400/06* (2013.01)

(58) Field of Classification Search
None
See application file for complete search history.

(56) References Cited

U.S. PATENT DOCUMENTS

| 3,697,652 A | 10/1972 | Rovati et al. |
|---|---|---|
| 4,216,204 A | 8/1980 | Robertson |
| 4,782,046 A | 11/1988 | Brown et al. |
| 4,801,619 A | 1/1989 | Lindblad |
| 4,808,576 A | 2/1989 | Schultz et al. |
| 4,837,024 A | 6/1989 | Michaeli |
| 5,141,928 A | 8/1992 | Goldman |
| 5,364,845 A | 11/1994 | Henderson |
| 5,442,053 A | 8/1995 | della Valle et al. |
| 5,466,823 A | 11/1995 | Talley et al. |
| 5,498,606 A | 3/1996 | Soll et al. |
| 5,587,363 A | 12/1996 | Henderson |
| 5,756,529 A | 5/1998 | Isakson et al. |
| 5,840,715 A | 11/1998 | Florio |
| 5,916,565 A | 6/1999 | Rose et al. |
| 5,929,050 A | 7/1999 | Petito |
| 6,127,356 A | 10/2000 | Crapo et al. |
| 6,271,213 B1 | 8/2001 | Henderson et al. |
| 6,432,929 B1 | 8/2002 | Stone |
| 6,492,349 B1 | 12/2002 | Henderson |
| 6,583,123 B2 | 6/2003 | Henderson et al. |
| 6,632,804 B2 | 10/2003 | Ekanayake |
| 6,645,948 B2 | 11/2003 | Petito et al. |
| 6,906,044 B2 | 6/2005 | Hermido |
| 6,949,525 B2 | 9/2005 | Hermida |
| 2003/0216348 A1 | 11/2003 | Henderson et al. |
| 2004/0092479 A1* | 5/2004 | Marcum .......................... 514/54 |
| 2004/0166096 A1* | 8/2004 | Kolkin et al. ................. 424/93.7 |
| 2004/0253212 A1 | 12/2004 | Koiwai et al. |

(Continued)

FOREIGN PATENT DOCUMENTS

| EP | 0509120 A1 | 10/1991 |
|---|---|---|
| EP | 1 762 247 A1 | 3/2007 |

(Continued)

OTHER PUBLICATIONS

Gimble et al. Cytotherapy (2003) vol. 5, No. 5, 362-369.*

(Continued)

*Primary Examiner* — Layla Bland
(74) *Attorney, Agent, or Firm* — Sutherland Asbill & Brennan LLP

(57) ABSTRACT

A pharmaceutical preparation for treating connective tissue damage in man and in animals, comprising a therapeutically effective amount of a glycosaminoglycan composition comprising chondroitin sulfate, N-acetyl D-glucosamine, and hyaluronan, in combination with isolated stem cells. Methods of use and kits containing the glycosaminoglycan composition and materials for isolating stem cells and for treating connective tissue damage and repair of cartilage in man and in animals are also provided.

13 Claims, No Drawings

(56) References Cited

U.S. PATENT DOCUMENTS

2006/0045872 A1    3/2006   Miguel et al.
2008/0003257 A1*   1/2008   Marcum et al. .............. 424/426

FOREIGN PATENT DOCUMENTS

GB          2317109 A       3/1998
WO       2004/034980 A2     4/2004

OTHER PUBLICATIONS

PCT International Search Report dated Sep. 11, 2008 for PCT/US2008/67699 (2 pages).
Bucci et al., 2005, "P196 Comparison Between Glucosamine with Chondroitin Sulfate and Glucosamine with Chondroitin Sulfate with Hyaluronate for Symptoms of Knee Osteoarthritis," Ostheoarthritis and Cartilage, 13:S99.
European Supplementary Search Report dated Aug. 31, 2010 for EP Application No. 08771608.0 (2 pages).
Bassleer et al., 1998, "Stimulation of Proteglycan Production by Glucosamine Sulfate in Chondrocytes Isolated from Human Osteoarthritic Articular Cartilage in Vitro," Osteoarthritis and Cartilage, vol. 6, pp. 427-434.
Bucci et al., 1994, "Glucosamine Salts and Chondroitin Sulfates," Townsend Letter for Doctors, pp. 52-54.
Capps et al., 1966, "Hexosamine Metabolism," Biochimica et Biophysica ACTA, 127:194-204.
Coleman et al., 1999, "Characterization of the Effect of High Molecular Weight Hyaluronan on Trans-Synovial Flow in Rabbit Knees," Journal of Physiology, 514.1, pp. 265-282.
Coleman et al., 1997, "Hyaluronan Secretion into the Synovial Cavity of Rabbit Knees and Comparison with Albumin Turnover," Journal of Physiology, 503.3, pp. 645-656.
Coleman et al., 2000, "Role of Hyaluronan Chain Length in Buffering Interstitial Flow Across Synovium in Rabbits," Journal of Physiology, 526.2, pp. 425-434.
Day et al., 2002, "Hyaluronan-Binding Proteins: Tying up the Giant," The Journal of Biological Chemistry, vol. 277, No. 7, pp. 4585-4588.
Dorna et al., 1998, "Effects of Oral and Intramuscular Use of Chondroitin Sulfate in Induced Equine Aseptic Arthritis."
Hinderlich et al., 2000, "Molecular Cloning and Characterization of Murine and Human N-acetylglucosamine Kinase," Eur. J. biochem., 267:3301-3308.
Johnson et al., 2001, "Chondroitin Sulfate," Continuing Education Module from the New Hope Institute of Retailing.
McIlwraith, "Traumatic Joint Injuries and Disease," http://www.equineortho.colostate.edu/questions/tjd.htm, Jun. 2007.
Murray M.:"Glucosamine sulfate: effective osteoarthritis treatment." Amer. J. Nat. Med. 1994; Sep. 10-14.
Sabaratnam et al., 2002, "Interactive Effect of Chondroitin Sulphate C and Hyaluronan on Fluid Movement Across Rabbit Synovium," Journal of Physiology, 540.1, pp. 271-284.
Schiavinato et al., 2002, "Comparison of the Effects of Intra-Articular Injections of Hyaluronan and Its Chemically Cross-Linked Derivative (Hylan G-F20) in Normal Rabbit Knee Joints," Clinical and Experimental Rheumatology, 20:445-454.
Shikhman et al., 2001, "N-Acetylglucosamine Prevents IL-1beta-Mediated Activation of Human Chondrocytes," The American Association of Immunologists.
Tersariol et al., 2002, "Proteinase Activity Regulation by Glycosaminoglycans," Brazilian Journal of Medical and Biological Research, 335:135-144.
Tesoriere et al., 1972, "Intestinal Absorption of Glucosamine and N-Acetylglucosamine," Experientia 28:770-1.
Todhunter et al., 1993, "Effects of Exercise and Polysulfated Glycosaminoglycan on Repair of Articular Cartilage Defects in the Equine Carpus," Journal of Orthopaedic Research, 11:782-795.
Heart et al., 2002, "Glucose Transport by Osmotic Shock and Vanadate is Impaired by Glucosamine," Biochem Biophys Res Commun; 292:308-11.
de Mattei et al., 2002, "High Doses of Glucosamine-HC1 have Detrimental Effects on Bovine Articular Cartilage Explants Cultured in vitro," Osteoarthritis-Cartilage.; 10(10):816-25.
Breborowicz et al., 1998, "The effect of N-acetylglucosamine as a substrate for in vitro synthesis of glycosaminoglycans by human peritoneal mesothelial cells and fibroblasts," Adv Perit Dial; 14:31-5.
Barclay et al., 1998, "Glucosamine," The annals of Pharmacotherapy, 32(5):574-579.
Bertone, 1996, "Infectious Arthritis," Joint Disease in the Horse, W.B. Sanders, pp. 397-409 (ISBN 0-7216-5135-6).
Vidal et al., 1978, Pharmocol. Res. Commun., 10:557-569.
Maini et al., 1995, "Aetiopathogenesis of Rheumatoid Arthritis, in Mechanisms and Modes of Rheumatoid Arthritis," Academic Press Ltd., pp. 25-46.
Hesse, 1987, "The Occurrence of Elastic System Fibres in the Matrix of Normal Articular Cartilage," Tissue Res, 248:589-593.

* cited by examiner

GLYCOSAMINOGLYCAN COMPOSITIONS IN COMBINATION WITH STEM CELLS

CROSS-REFERENCE TO RELATED APPLICATIONS

This patent application is a continuation in part of U.S. Ser. No. 11/766,510 filed Jun. 21, 2007, pending, which is incorporated herein by reference in its entirety.

FIELD OF INVENTION

The present invention is generally directed to a pharmaceutical preparation, and methods of use thereof, for treating connective tissue damage and repairing cartilage in man and in animals. More particularly, the present invention provides a pharmaceutical preparation comprising a glycosaminoglycan composition comprising one or more glucosaminoglycans (GAGs) in combination with stem cells or a pharmaceutically acceptable formulation comprising stem cells for use in treating connective tissue disorders and repairing cartilages.

BACKGROUND OF THE INVENTION

The four primary types of vertebrate tissues are epithelial tissue, muscle tissue, nerve tissue, and connective tissue. Connective tissues are typically involved in structure and support, and are usually derived from mesoderm cells. Connective tissue is widespread in the body, and as the name implies, it primarily serves a connecting function to bind or strengthen organs or other tissues. It also functions inside the body to divide and compartmentalize other tissue structures.

In vertebrates, the most common type of connective tissue is loose connective tissue. Loose connective tissue holds organs in place and attaches epithelial tissue to other underlying tissues. Loose connective tissue is named based on the "weave" of its constituent fibers. There are three main component types of loose connective tissue: collagenous fibers, elastic fibers, and reticular fibers. Collagenous fibers are made of collagen and consist of bundles of fibrils that are coils of collagen molecules. Elastic fibers are made of elastin and are stretchable. Reticular fibers join connective tissues to other tissues. Loose connective tissue also includes adipose tissue that stores fat.

Another type of connective tissue is fibrous connective tissue, which is found in tendons and ligaments. Fibrous connective tissue is composed of large amounts of closely packed collagenous fibers. Cartilage is a form of fibrous connective tissue that is composed of closely packed collagenous fibers in a rubbery gelatinous substance called chondrin. The skeletons of sharks are composed of cartilage. Cartilage also provides flexible support for certain structures in humans including the nose, trachea, ears, and articulating joints, for example.

Bone and blood are two other specialized connective tissues. Bone is a type of mineralized connective tissue that contains collagen and calcium phosphate, a mineral crystal. Calcium phosphate gives bone its firmness. Blood is also considered a type of connective tissue. Even though it has a different function in comparison to other connective tissues it does have an extracellular matrix. The matrix is the plasma and erythrocytes, leukocytes and platelets are suspended in the plasma.

The connective tissues of humans and animals are constantly subjected to stresses and strains from mechanical forces and from diseases that can result in afflictions, such as arthritis, joint inflammation stiffness and connective tissue injuries such as tendonitis, bursitis, strained or torn ligaments and tendons and the like. Indeed, connective tissue afflictions are quite common, presently affecting millions of people and animals. Further, such afflictions can be not only painful but, in their extreme, debilitating.

Arthritic diseases, characterized by pain, inflammation and stiffness of the joints leading to reduced range of mobility, are due to the degradation of connective tissue (mainly cartilage) in joints. Such diseases particularly affect weight-bearing joints such as the hips, knees, spine, ankles and feet and those joints with frequent movement such as hands, arms and neck. For instance, osteoarthritis (OA) in particular is a degenerative disease of the joint cartilage resulting in narrowing of the joint space and changes in the underlying bone (Barclay, et al., The Annals of Pharmacotherapy, (May, 1998) 32: 574-79). Osteoarthritis is the most common form of arthritis and it affects approximately one in ten people in North America. Osteoarthritis is not limited to humans, but occurs in other mammals such as horses, dogs, cats, mice and guinea pigs as well, making osteoarthritis one of the most common sources of chronic pain seen by veterinarians.

Rheumatoid arthritis (RA) is a connective tissue disease that has some similar symptoms to osteoarthritis. Rheumatoid arthritis is among the most debilitating of all forms of arthritis, causing joints to ache and throb and eventually become deformed. Sometimes these symptoms make even the simplest daily activities difficult to manage. The exact cause of rheumatoid arthritis is unknown, however, it is believed to be an autoimmune disease (Maini, et al., Aetiopathogenesis of Rheumatoid Arthritis. in Mechanisms and Modes of Rheumatoid Arthritis, (1995) Academic Press Ltd. pp. 25-46), in which the immune system attacks body tissues, e.g., the synovium, as if they were foreign invaders, culminating in inflammatory and destructive responses in joints as well as other tissues. It has also been postulated that rheumatoid arthritis is triggered by an infection, possibly a virus or bacterium in people with an inherited susceptibility. Some researchers also believe that hormones may be involved in the development of rheumatoid arthritis.

As with some other forms of arthritis, rheumatoid arthritis involves inflammation of the joints. In rheumatoid arthritis, white blood cells, whose usual job is to attack unwanted invaders, such as bacteria and viruses, move from the bloodstream into the synovium. Here, these blood cells appear to play an important role in causing the synovial membrane to become inflamed (synovitis). This inflammation results in the release of proteins that, over months or years, cause thickening of the synovium. These proteins can also damage cartilage, bone, tendons and ligaments. Gradually, the joint loses its shape and alignment and eventually, it may be destroyed.

Under normal conditions, the body maintains the synovial joint in state of homeostasis through a variety of complex hormonal and mechanical feedback mechanisms. Several types of insult or injury can upset the delicate homeostatic balance. For example, repeated trauma or stress (slow chronic insult) to the joint during everyday use, e.g., athletic training or performance, is often the inciting cause of joint inflammation and loss of homeostasis. Initially, such stress results in only soft tissue inflammation in the form of synovitis or capsulitis (e.g., traumatic synovitis). Cartilage damage may or may not initially be present in the early stages of stress related injury or inflammation. However, the release of inflammatory mediators into the joint such as prostaglandins, cytokines, lysosomal enzymes and free radicals can lead to damage of articular cartilage and can cause cartilage degradation and leading to development of degenerative joint disease (DJD).

A second type of insult or injury, the osteochondral defect, e.g., a chip fracture, is often associated with an acute mechanical failure or traumatic injury, e.g., an acute racing or training injury, although, such a fracture can be due to secondary complications associated with chronic DJD. Under this scenario, the lesion often starts as a traumatically induced defect in the articular cartilage. This may occur as a fragmentation of the original tissue from the joint margins or other defect which compromises the surface and integrity of the articular cartilage. Exposure of the supporting subchondral bone to synovial fluid and the intermittent pressures of the synovial fluid generated by repeated joint movement (repeated stress and trauma of training or racing) can lead to progressive subchondral bone sclerosis and eventual dislodging of the chip or bone fragment. Left untreated, the resulting damage often becomes progressive and DJD results (see, e.g., Nixon et al., "Equine Fracture Repair," W. B. Saunders Co., 1996 (ISBN 0-7216-6754-6)).

Under either scenario, once compromised, the damage to articular cartilage is usually permanent. In general, once damaged, therapy is normally directed at limiting or reducing joint inflammation, limiting the release of inflammatory mediators, removal of the inciting cause (e.g., the chip) and replacement of synovial fluid components. These measures are combined with a period of rest to allow for healing and fibrocartilage deposition at the affected area. The long term therapeutic objective is directed at slowing the progression of degenerative processes and controlling the clinical signs of DJD. Prevention is often aimed at limiting joint inflammation before damage to cartilage occurs and in providing proper nutritional support.

The treatment of connective tissue afflictions can be quite problematic. A simple decrease in the stress to which the connective tissue is subjected is often not an option, especially in the case of athletes and animals such as race horses. Consequently, treatment is often directed at controlling the symptoms of the afflictions and not their causes, regardless of the stage of the degenerative process. Presently, steroids, such as corticosteroids and NSAIDs, are widely used for the treatment of these ailments (Vidal, et al., Pharmocol. Res. Commun., 10:557-569 (1978)). However, drugs such as these, which inhibit the body's own natural healing processes, may lead to further deterioration of the connective tissue.

Connective tissue, for example articular cartilage, is naturally equipped to attempt to repair itself by manufacturing and remodeling prodigious amounts of collagen and proteoglycans (PGs). This ongoing process is placed under stress when an injury occurs. In such cases, the production of connective tissue matrix (collagen and proteoglycans) can double or triple over normal levels, thereby increasing the demand for the building blocks of both collagens and proteoglycans. The building blocks for collagen are amino acids, especially proline, glycine and lysine. Proteoglycans are large and complex macromolecules comprised mainly of long chains of modified sugars called glycosaminoglycans (GAGs) or mucopolysaccharides. The terms glycosaminoglycans and mucopolysaccharides are understood in the art to be interchangeable. Due to their dense negative ion content, proteoglycans molecules are able to attract and retain water within the cartilage formation specifically for lubrication. Proteoglycans provide the unique mechanical properties for flexibility, resiliency, and resistance to and recovery under compressive forces.

Glucosaminoglycans are polysaccharides which occur widely in the animal kingdom. Glucosaminoglycans that are present in the tissues of vertebrate animals have mainly a linear structure which is repetition of a disaccharide units composed of two monosaccharides. Five kinds of glucosaminoglycans are found in the tissues and fluids of vertebrates: chondroitin sulfates, keratin sulfates, dermatan sulfates, heparin sulfates, and hyaluronic acid.

Proteoglycans and collagen are the chief structural elements of all connective tissues. Their synthesis is essential for proper maintenance and repair of connective tissues. In vitro, the introduction of glucosamine, a key precursor for GAGs, has been demonstrated to increase the synthesis of collagen and GAGs in fibroblasts. In vivo, topical application of glucosamine has enhanced wound healing. Glucosamine has also exhibited reproducible improvement in symptoms and cartilage integrity in humans with osteoarthritis (L. Bucci, Nutritional Supplement Advisor, July 1992)).

The major glycosaminoglycans found in cartilage are chondroitin sulfate, dermatan sulfate, keratan sulfate and hyaluronic acid (also known as hyaluronan or HA). Heparin sulfate is also a glycosaminoglycan, although it is not a component of articular cartilage. Newer names for proteoglycans sometime reference function of the core protein within the molecule found in chondroitin sulfate and keratin sulfate, e.g., aggregan, a large proteoglycan aggregates with hyaluronin, or reference location (e.g., decorin (dermatan sulfate), which decorates type I collagen fibrils), or reference primary structure, biglycan which has two glysoaminoglycan chains. Chondrocytes are active cells within the cartilage matrix, which manufacture new collagen and proteoglycan molecules while excreting enzymes, which aid in removal of damaged cartilage and proteoglycans.

Chondroitin sulfate is broken down into sulfate disaccharides and N-acetyl galactosamine. Chondroitin sulfate, as CS4 and CS6 within the body, is thought to be an essential glycosaminoglycan which binds water to the articular cartilage matrix and is necessary for the formation of proteoglycans.

In particular, chondroitin sulfate is a long hydrophilic chain of repeating sugars. This glycosaminoglycan binds to proteoglycan molecules aiding in water and nutrient transportation within the articular cartilage. Chondroitin in its sulfate form includes galactosamine, a primary substrate of hylauronan and a disaccharide pathway for proteoglycan synthesis secondary to the hexosamine pathways utilized for glycosaminoglycan production. Chondroitin sulfate chains comprise the space formation of the cartilage matrix and integral parts of the proteoglycan molecule. Chondroitin stimulates the production of proteoglycans, glycosaminoglycans, and collagen, which are the building blocks of healthy cartilage. Chondroitin sulfate also inhibits the secretion of degenerative enzymes by the chondrocytes within articular cartilage. Chondroitin sulfates are non-toxic and work synergistically with glucosamine to hydrate and repair articular cartilage.

Hylauronan is an integral part of both synovial fluid and articular cartilage. Within the articular cartilage, hylauronan provides viscoelastic properties allowing ease of motion between opposing surfaces and increasing compressive resistance. Within the synovium, hylauronan, as a component of synovial fluid, provides an effective barrier regulating the introduction of plasma components. Under normal conditions, the body will synthesize sufficient amounts of base components to maintain and grow healthy articular cartilage, while limiting the production and release of destructive proteinases, inflammatory mediators and catabolic enzymes.

Glucosamine, as glucosamine 5-phosphate, is naturally occurring within the body and is a component in the biosynthesis of glycosaminoglycans, proteoglycans, hyaluronan, and collagen. Glucosamine is available in exogenous forms, glucosamine sulfate sodium, glucosamine hydrochloride and N-acetyl D-glucosamine. N-acetyl D-glucosamine is also a derivative of glucose obtained by chemical hydrolysis of chitin. This polysaccharide is readily soluble in water and extremely bioavailable. N-acetyl D-glucosamine binds to glucuronic acid as well as galactose making it a precursor to hyaluronic acid, keratan-sulfate and chondroitin sulfate. This unique derivative aids in proteoglycan, collagen and glycosaminoglycan production. N-acetyl D-glucosamine has also been shown to aid in the healing of soft tissue injury. D-Glucuronic acid is a key substrate comprising one half of the hyaluronan molecule, the other being N-acetyl D-glucosamine.

There have been countless therapeutic approaches for management of joint disease, providing nutritional supplementation of metabolic precursors to the diet to aid in the biosynthesis of proteoglycans, GAG's, hyaluronan, and collagen (see, U.S. Pat. Nos. 5,364,845 and 5,587,363). Numerous other disclosures also suggest the introduction of nutritional supplements as therapy for the treatment of connective tissues. For instance, U.S. Pat. No. 3,683,076 to Rovati et al. teaches that glucosamine sulfates are useful to treat arthritic conditions. U.S. Pat. No. 3,697,652 to Rovati et al. discloses that N-acetyl glucosamine can be used to treat degenerative afflictions of the joints. U.S. Pat. Nos. 5,364,845, 5,587,363, 6,492,349, 6,271,213, and 6,583,123 to Henderson et al. teach that glucosamine, chondroitin, manganese, and/or S-Adenosylmethionine (SAM) are used to protect and repair connective tissue. U.S. Pat. No. 6,632,804 to Ekanauake teaches that ferrous ion and an ascorbate, and glucodamine derivative are useful in treating osteoarthritis. U.S. Pat. No. 6,645,948 to Prtito et al. teaches a nutritional composition for treating connective tissue including a glucosamine salt, chondroitin sulfate, collagen and sodium hyaluronate.

In U.S. Pat. No. 5,840,715 to Florio, N-acetyl glucosamine sulfate, chondroitin sulfate, gamma linolenic acid ercosapentaenoic acid and docosahexaneoic acid, and manganese aspartate are combined to treat arthritis symptoms. U.S. Pat. No. 5,916,565 to Rose et al. teaches a composition comprised of D-glucosamine hydrochloride, chondroitin sulfate, cayenne, ginger, turmeric, yucca, Devil's Claw, nettle leaf, Black Cohosh, alfalfa, and celery seeds to repair and maintain damaged tissues in joints of vertebrates. In U.S. Pat. No. 5,922,692, Marino discloses that glucosamine sulfate and chondroitin sulfate can be added to foodstuffs. Additional related art discloses pharmaceutical compositions and methods for the treatment of connective tissue in humans and animals, such as U.S. Pat. Nos. 4,216,204, 4,782,046, 4,808,576, 4,837,024, 5,141,928, 5,840,715, 5,442,053, and 5,929,050.

Stem cells are cells found in most multi-cellular organisms. They are capable of retaining the ability to reinvigorate themselves through mitotic cell division and can differentiate into a diverse range of specialized cell types. The two broad types of mammalian stem cells are: embryonic stem cells that are found in blastocysts, and adult stem cells that are found in adult tissues. The two classical properties of stem cells are self-renewal and potency. Self-renewal refers to the ability to go through numerous cycles of cell division while maintaining the undifferentiated state, and potency refers to the capacity to differentiate into specialized cell types. Potency specifies the differentiation potential to differentiate into different cell types of the stem cells. For instance, totipotent stem cells are cells produced from the fusion of an egg and sperm cell, as well as the first few divisions of the fertilized egg, and they can differentiate into embryonic and extra-embryonic cell types. Pluripotent stem cells are the descendants of totipotent cells and can differentiate into cells derived from any of the three germ layers. Multipotent stem cells can produce only cells of a closely related family of cells (e.g. hematopoietic stem cells differentiate into red blood cells, white blood cells, platelets, etc.). Unipotent cells can produce only one cell type, but have the property of self-renewal which distinguishes them from non-stem cells (e.g. muscle stem cells). All such forms of stem cells can be considered to be progenitor cells which are not terminally differentiated.

Progenitor cells refer to immature or partially undifferentiated cells, typically found in post-natal animals Like stem cells, progenitor cells have a capacity for self-renewal and differentiation, although these properties may be limited depending upon the type of cell. Embryonic stem cells are true stem cells in that they are pluripotent and show unlimited capacity for self-renewal. In contrast, many cells termed adult stem cells are more commonly termed progenitor cells, as their capacities for unlimited self renewal and plasticity have not been comprehensively demonstrated. The majority of progenitor cells lie dormant or possess little activity in the tissue in which they reside. They exhibit slow growth and their main role is to replace cells lost by normal attrition. Upon tissue damage or injury, progenitor cells can be activated by growth factors or cytokines, leading to increased cell division important for the repair process. Examples of progenitor cells include satellite cells found in muscle and the transit-amplifying neural progenitors of the rostral migratory stream. Bone marrow stromal cells, basal cell of epidermis have 10% of progenitor stem cell, although they are often classed as stem cells due to their high plasticity and potentially unlimited capacity for self renewal.

Periosteum is a membrane that lines the outer surface of all bones, except at the joints of long bones. Endosteum lines the inner surface of all bones. Periosteum consists of the irregular type of dense connective tissue. Periosteum is divided into an outer "fibrous layer" and inner "cambium layer". The fibrous layer contains fibroblasts while the cambium layer contains progenitor cells which develop into osteoblasts. These osteoblasts are responsible for increasing the width of a long bone, and the overall size of the other bone types. After a bone fracture, the progenitor cells develop into osteoblasts and chondroblasts which are essential to the healing process. As opposed to osseous tissue, periosteum has nociceptive nerve endings, making it very sensitive to manipulation. It also provides nourishment by providing the blood supply. Periosteum is attached to bone by strong collagenous fibers called Sharpey's fibres, which extend to the outer circumferential and interstitial lamellae. It also provides an attachment for muscles and tendons.

Mesenchymal stem cells or Marrow Stromal Cells (MSCs) are multipotent stem cells that can differentiate into a variety of cell types, except hematopoietic cells. Cell types that MSCs have been shown to differentiate into in vitro or in vivo include osteoblasts, chondrocytes, myocytes, adipocytes, and beta-pancreatic islets cells. Like the connective tissue cells, Stromal cells, MSCs also provide the supportive structure in which the functional cells of the tissue reside. In addition, MSCs play roles in repair of tissue. Because MSCs can encompass multipotent cells derived from other non-marrow tissues, such as adult muscle side-population cells or the Wharton's jelly present in the umbilical cord, as well as in the dental pulp of deciduous baby teeth, yet do not have the capacity to reconstitute an entire organ, MSCs may also stand for Multipotent Stromal Cells.

Because in adult organisms, stem cells and progenitor cells act as a repair system for the body, replenishing specialized cells, but also maintain the normal turnover of regenerative organs, these cells have been utilized for treating skeletal and other connective tissue disorders. For instance, U.S. Pat. Nos. 5,226,914; 5,197,985; 5,735,542; and 6,010,696 to Caplan et al. provide methods and devices for treating and repairing connective tissue damage by enhancing bone marrow or hematopoietic progenitor cell engraftment and implantation and differentiation of marrow-derived mesenchymal cells by applying culturally expanded purified marrow-derived mesenchymal cells to an area of connective tissue damage under conditions suitable for differentiating the cells into the type of connective tissue necessary for repair, and methods and devices for using the purified marrow-derived mesenchymal cells in order to enhance the production of hematopoitic cells.

Mesenchymal stem cells are the formative pluripotent blast cells found in the bone that are capable of differentiating into any of the specific types of connective tissues (i.e., the tissues of the adipose, areolar, osseous, cartilaginous, elastic, and fibrous connective tissues) depending upon various environmental influences. Although these cells are normally present at very low frequencies in bone marrow and other mesenchymal tissues, a process for isolating, purifying, and greatly replicating the mesenchymal stem cells in culture is described in U.S. Pat. No. 5,486,359. Under selected conditions, the mesenchymal stem cells can be induced to differentiate into different types of skeletal and connective tissues such as bone, cartilage, tendon, ligament, muscle, other connective tissues and marrow stroma.

Moreover, U.S. Pat. No. 5,842,477 provides methods of making and/or repairing cartilage in vivo by implanting into a patient, at a site of cartilage damage or loss, a biocompatible, non-living three-dimensional scaffold or framework structure in combination with periostel/perichondrial tissue, and administering a preparation of chondrocytes and/or other stromal cells, such as chondrocyte progenitor cells, to the site of the implant before, during or after implantation of the scaffold and/or the periosteal/perichondrial tissue. It is provided that the periosteal/perichondrial tissue can be used to hold the scaffold in place at the site of implantation and also provides a source of stromal cells, e.g., chondrocytes and/or chondrocyte progenitor cells, for attachment to the scaffold in vivo, and the seeded stromal cells provides not only a readily-accessible source of chondrocytes and/or other stromal cells for attachment to the scaffold but also provides a rapid and efficient means of inducing chondrogenesis as well as migration of stromal cells from the surrounding in vivo environment to the scaffold via factors produced by the stromal cells of the preparation. Additionally, it is provided that the seeded stromal cells can be genetically engineered to express gene products beneficial to growth, implantation and/or amelioration of disease conditions, resulting in the efficient production of new cartilage in vivo, that is useful in the production/repair of articular cartilage in patients suffering from degenerative connective tissue diseases such as rheumatoid and/or osteoarthritis as well as in patients who have cartilage defects due to trauma.

Furthermore, U.S. Pat. No. 6,936,281 to Seshi provides isolated pluri-differentiated human mesenchymal progenitor cells (MPCs) from Dexter-type cultures, and method of isolating and using these cells for diagnostic uses, and for therapeutic uses to enhance the engraftment of hematopoietic progenitor cells, enhance bone marrow transplantation, or aid in the treatment or prevention of graft-versus-host diseases (GvHD).

While all the above references have been described as being effective for their intended use, there remains a need in the art for a therapeutic composition which demonstrates enhanced effectiveness in the treatment of connective tissues, exhibits other improved beneficial properties, and provides even wider applications. The present invention meets these needs at least in part.

SUMMARY OF THE INVENTION

The present invention provides an enhanced effectiveness in the preventing and treating connective tissue damage, or specifically in the repair of cartilage in an affected site. In one embodiment, the present invention provides a pharmaceutical preparation, and method of use thereof, for treating connective tissue damage and for repair cartilage in an affected site in man and in animals. The pharmaceutical preparation described herein comprises a glycosaminoglycan composition in combination with stem cells. Methods of treatment are provided herein using the glycosaminoglycan composition in combination with stem cells, either as a pharmaceutically acceptable admixture or in concurrent or sequential administration. The glycosaminoglycan compositions have further utility in combination with stem cells as a culture media and as a cryoperservative.

As used herein, the glycosaminoglycan composition described herein comprises one or more glucosaminoglycans (GAGs) and is formulated into any pharmaceutically acceptable formulations, including, but not limited to, a sterile solution, suspension or gel for direct application or intra-articular, intramuscular, intravenous, or other parenteral or systemic administration. Any GAGs can be included in the glycosaminoglycan composition described herein. In certain embodiments, the glycosaminoglycan composition comprises, or consists essentially of, chondroitin sulfate, glucosamine, and hyaluronan. In certain embodiments, the glycosaminoglycan composition comprises, or consists essentially of, glucosamine and hyaluronan.

In one embodiment, the glycosaminoglycan composition comprises a mixture of chondroitin sulfate, glucosamine and hyaluronan, and can be stored in a single container at room temperature, in a refrigerator or a freezer. In yet another embodiment, the glucosamine, such as N-acetyl D-glucosamine, is stored in a separate container at room temperature, in a refrigerator or freezer, and can be mixed with the chondroitin sulfate and hyaluronan mixture before administration. In yet another embodiment, the glycosaminoglycan composition comprises chondroitin sulfate, hyaluronan, and glucosamine, such as N-acetyl D-glucosamine, all mixed together and stored in a single container ready for administration. In yet another embodiment, the glycosaminoglycan composition is the POLYGLYCAN® composition (Arthro-Dynamic Technologies, Lexington, Ky.) consisting essentially of a therapeutically effective amount of chondroitin sulfate, N-acetyl D-glucosamine, and hyaluronan (hyaluronic acid) which is combined with a stem cell preparation for culturing or cryopreserving the stem cells, or for therapeutically preventing or treating connective tissue damage.

In the joint, for example, chondroitin sulfate acts to stimulate the production of proteoglycans, glycosaminoglycans, and collagen, inhibits degenerative enzymes excreted by the chondrocytes, and synoviocytes, and aids in nutrient transportation within the synovial fluid. Glucosamine, in particular N-acetyl D-glucosamine, increases the synoviocyte and chondrocyte production and subsequent availability of endogenous hyaluronan by the direct in situ inclusion of its prime substrates galactosamine (through chondroitin sulfate assimilation) and N-acetyl D-glucosamine. The exogenous hyaluronan acts to replace depleted endogenous hyaluronan and to lubricate and coat healthy as well as damaged articular tissue during the reparative process. The above modes of action are believed accurate; however, the claimed uses of the present compositions are not limited to such hypothesized mechanisms of activity for achieving efficacy.

In one embodiment, the chondroitin sulfate in the composition is chondroitin 4-sulfate (CS4), chondroitin 6-sulfate (CS6), or a mixture of both CS4 and CS6. A therapeutically effective amount of chondroitin sulfate and N-acetyl D-glucosamine can be from between about 0.5 grams to about 1.5 grams of per unit dose, respectively, and the therapeutically effective amount of hyaluronan can be from about 10 mg to about 50 mg per unit dose.

In yet other embodiments, the stem cells are cultured or frozen with one or more appropriate cryoprotectants including the glycosaminoglycan compositions described herein. As used herein, the term "stem cells" refers to cells which are not terminally differentiated, including cells capable of retaining the ability to be passaged through mitotic cell division, and ultimately differentiating into a diverse range of specialized cell types, including, but not limited to, loose, dense regular, and elastic connective tissue cell types. In one embodiment, the stem cells described herein are presursors to mesenchyme and/or stromal cells including, but not limited to, osteoblasts, chondrocytes, chondrocyte progenitor cells including mesenchymal stem cells or MSCs, fibroblasts, fibroblast-like cells, and other stromal cells capable of producing collagen types and proteoglycans which are typically produced in cartilaginous tissues. In yet another embodiment, the stem cells described herein are stromal cells capable of producing adipose or adipose-like cells for adipose. In yet another embodiment, the stem cells described herein are mesenchyme that differentiates into hematopoietic tissue.

In yet another embodiment, the stem cells are chondroigenic stem and/or progenitor cells including mesenchymal stem cells or MCSs. In further embodiments, the mesenchymal stem cells or MCSs are human mesenchymal stem cells isolated from a human tissue specimen. In yet other embodiments, the mesenchymal stem cells or MCSs are animal mesenchymal stem cells isolated from an animal tissue specimen. In yet other embodiments, the chondroigenic stem and/or progenitor cells can be obtained from the patient (or animal subject) or a histocompatible donor. The chondrocytes, progenitor cells, fibroblast-like cells and other cells and/or elements that comprise the stroma may be fetal or adult in origin, and may be derived from convenient sources such as adipose, cartilage, bone, skin, ligaments, tendons, muscles, placenta, umbilical cord, etc. For example, stromal cells such as chondrocytes may be derived from any type of cartilage, including but not limited to, hyaline cartilage, costal cartilage, fibrous cartilage, etc., which can be obtained by biopsy (where appropriate) or upon autopsy.

Chondrocyte progenitor cells may be derived from various sources including bone marrow, periosteum, perichondrium or various sources of undifferentiated human mesenchyme. Fibroblasts can be obtained in quantity rather conveniently from foreskin, preferably fetal foreskin, or, alternatively, any appropriate cadaver organ. Fetal cells, including fibroblast-like cells and chondrocyte progenitor cells, may be obtained from umbilical cord or placenta tissue or umbilical cord blood. Stem cells from a variety of sources may be used in the present invention, including stromal cells derived from cells of fetal origin which may be viewed as "universal donors" so as to minimize the risk of immunological rejection, or adult origin, particularly in the case of autologous cell isolation and transplantation.

The stem cells used in the present invention may be readily isolated by disaggregating an appropriate tissue and/or embryo which is to serve as the source of the cells. Once the tissue and/or embryo has been reduced to a suspension of individual cells, the suspension can be fractionated into subpopulations from which precursors of chondrocytes, fibroblasts and/or other stromal cells can be obtained. Furthermore, once chondrocytes or chondrocytes progenitor cells have been isolated, their population can be expanded mitotically in vitro in order to obtain the cell preparation for the combination with the other glucosaminoglycans in the composition disclosed in the present invention. The stem cells used in the present invention may be isolated and/or purified from the cultured primary and/or transferred or "passaged" cells. Moreover, once the stem cells of the present invention have been established in culture, they may be maintained or stored in cell "banks" comprising either continuous in vitro cultures of cells requiring regular transfer, or cells which have been cryopreserved. In one embodiment, the embryos and the stem cells provided herein are cultured in the glycosaminoglycan compositions described herein, and/or frozen in the presence of one or more suitable cryoprotectant, including the glycosaminoglycan compositions described herein, so that the stem cells provided herein are properly protected during the cryopreservation process, yielding improved viability. The cryoprotected stem cells constitute a bank of cells, portions of which can be "withdrawn" by thawing and then used for preparing the pharmaceutical preparation described herein.

The stem cells used in the present invention may be genetically engineered to produce gene products that promote the successful production or repair of cartilage or other connective tissue at a defect site or for use in gene therapies. The stem cells used in the present invention may also be genetically engineered to express one or more genes that would exert a therapeutical effect, or replace deficient genes in a patient or animal for gene replacement therapy. Furthermore, the stem cells used in the present invention may also be genetically engineered to knock out expression of factors that promote inflammation, rejection, or other undesired side effects at a defect site.

The present invention further provides that the stem cells used in the present invention further comprise other cells aid in the production of connective tissues and/or cartilage. For example, other cells found in loose connective tissue may be included along with chondrocytes or fibroblasts. Such cells include, but are not limited to, endothelial cells, pericytes, macrophages, monocytes, plasma cells, mast cells, and adipocytes. As used herein, the connective tissue types include, but are not limited to, bone, cartilage, tendon, ligament, dermis, periosteum, perichondrium, skin, or adipose.

As used herein, the pharmaceutical preparation of the present invention is formulated in a suitable form, including, but not limited to, a form of sterile solution, suspension, or a gel or paste-like formulation. In one embodiment, the glycosaminoglycan composition described herein can be applied directly (e.g., direct injection) into the affected connective tissue, e.g., a joint, a tendon, a ligament or bone, followed by subsequent direct application of the stem cells or the pharmaceutical acceptable formulations comprising the stem cells. In yet other embodiments, the pharmaceutical preparation of the present invention may be formulated for intra-articular and/or systemic or parenteral administration, in which the glycosaminoglycan composition and the stem cells or a pharmaceutical acceptable formulation comprising the stem cells may be administered either separately, or mixed together immediately before administration. Systemic administrations can include, but are not limited to, intramuscular, intravenous or subcutaneous injection.

In yet another embodiment, each of the pharmaceutical preparation, the glycosaminoglycan composition, the stem cells, or the formulation comprising the stem cells of the present invention can be attached to a sheet of material adapted for implantation onto or between tissues of a mammalian body. Each of the pharmaceutical preparation, the glycosaminoglycan composition, the stem cells, or the pharmaceutically acceptable formulation comprising the stem cells can be impregnated into a porous gauze-like material or coated onto a gauze-like material or joined to the material by adhesion and/or capillary action. The material may be either a permanent implant or it may be biodegradable. In yet another embodiment, each of the pharmaceutical preparation, the glycosaminoglycan composition, the stem cells, or the pharmaceutical acceptable formulation comprising the stem cells is attached to a bandage or other surgical materials, including, but not limited to, surgical suture material, surgical staple, or a device such as a buckle.

The pharmaceutical preparation described herein further may optionally comprise one or more other therapeutic agents, including, but not limited to, synthetic and non-synthetic corticosteroid agents, nonsteroidal anti-inflammatory drugs, analgesics, antirheumatics, immunoregulators, immunosuppressant, articular function augmenters, interleukin production inhibitors, or grow factor, all of which have therapeutic effects. Any drugs, agents, compounds, known and/or to be developed, showing any desired therapeutic effects are within the scope of this invention. In other embodiments, the invention may specifically exclude one or more of the above therapeutic agents. In yet another embodiment, the stem cells, or the pharmaceutically acceptable formulation comprising the stem cells, may further comprise other cells that aid in the production of one or more connective tissue. These other cells include, but are not limited to, endothelial cells, pericytes, macrophages, monocytes, plasma cells, mast cells, or adipocytes.

The present invention provides that the pharmaceutical preparation described herein enhances effectiveness promoting healthy growth of connective tissue and in the treatment and repair of connective tissue damage. As used herein, the term "connective tissue" refers to loose, dense regular, and elastic connective tissues. The loose connective tissues comprises constituent fibers including, but not limited to, collagenous fibers, elastic fibers, reticular fibers. The loose connective tissue also refers to an adipose tissue. The dense regular connective tissues include, but are not limited to, tendons, ligaments, cartilage, skeleton, and other fibrous connective tissues. The connective tissues used herein also refer to blood.

The present invention further provides that the pharmaceutical preparation described herein can be used in the prevention, treatment, and repair of connective tissue damage, which includes any primary or secondary diseases or injuries to the connective tissues in humans or animals. Such diseases or injuries include, but are not limited to, arthritic diseases, osteoarthritis (OA), rheumatoid arthritis (RA), osteochondrosis dessicans (OCD), cartilage damage, joint injuries, joint inflammation, joint synovitis, degenerative joint disease (DJD), post surgical DJD, traumatic injuries, fractures, tendon damage, ligament damage, skeletal damage, musculoskeletal damage, bone damage, fiber damage, adipose tissue damage, blood cell damage, and plasma damage.

The present invention further provides a method for preventing, treating, and repairing connective tissue damage in humans or in animals comprising administering to a man or animal in need thereof, a pharmaceutical preparation of the present invention. In one embodiment, the pharmaceutical preparation described herein comprises a glycosaminoglycan composition comprising, or consisting essentially of, a therapeutically effective amount of chondroitin sulfate, glucosamine, e.g., N-acetyl D-glucosamine, and hyaluronan, in combination with stem cells and/or a pharmaceutically acceptable formulation comprising the stem cells. In yet another embodiment, the pharmaceutical preparation described herein comprises POLYGLYCAN® composition that consists essentially of chondroitin sulfate, N-acetyl D-glucosamine, and hyaluronan, in combination with stem cells and/or a pharmaceutically acceptable formulation comprising the stem cells. In one embodiment, the stem cells described herein are progenitor mesenchymal or stromal cells including, but not limited to, osteoblasts, chondrocytes, including mesenchymal stem cells or MSCs, fibroblasts, fibroblast-like cells, and other stromal cells capable of producing collagen types and proteoglycans which are typically produced in cartilaginous tissues. In yet another embodiment, the stem cells described herein are stromal cells capable of producing adipose or adipose-like cells for adipose. In yet another embodiment, the stem cells described herein are mesenchymal that differentiate into hematopoietic tissue.

In one embodiment, the present invention provides that the pharmaceutical preparation described herein comprises a mixture of the glycosaminoglycan composition and the stem cells and/or the stem cell formulation in a suitable container for a period of time without degradation of each ingredient in the proteoglycan position and the stem cells. In one embodiment, the present invention provides that the pharmaceutical preparation described herein comprises the glycosaminoglycan composition and the stem cells or the stem cell formulation comprising the stem cells, in which the glycosaminoglycan composition and the stem cells or the stem cell formulation are mixed immediately before administering to the patient (human or animal subject) in need. In alternative embodiments, the stem cells or the stem cell formulation described herein can be administered before, during or after the administration of the glycosaminoglycan composition described herein.

DETAILED DESCRIPTION OF THE INVENTION

Additional objects, advantages and other novel features of the invention will be set forth in part in the description that follows and in part will become apparent to those skilled in the art upon examination of the foregoing or may be learned with the practice of the invention. Additionally, throughout this document, various publications and patents have been cited, the contents of which are incorporated herein by reference in their entirety.

Set forth in greater detail below are specific details related to a pharmaceutical preparation which demonstrates enhanced effectiveness in the treatment of connective tissue damage. The pharmaceutical preparation provided herein comprises a glycosaminoglycan composition comprising a therapeutically effective amount of chondroitin sulfate, a suitable glucosamine derivative, e.g., N-acetyl D-glucosamine, and a suitable hyaluronan (hyaluronic acid), in combination with stem cells or a pharmaceutically acceptable formulation comprising the stem cells.

Preparation of the Glycosaminoglycan Composition

The present invention provides that the pharmaceutical preparation described herein comprises a glycosaminoglycan composition. As used herein, the term "glycosaminoglycan composition" refers to any pharmaceutically acceptable composition comprising one or more glucosaminoglycans (GAGs), or pharmaceutically acceptable salts thereof, with or without a pharmaceutically acceptable carrier. The glycosaminoglycans can be selected from the group selected from, or consisting essentially of, chondroitin sulfate and hyaluronan. In one embodiment, the glycosaminoglycan composition described herein comprises chondroitin sulfate and hyaluronan, and optionally N-acetyl D-glucosamine. In one embodiment, the glycosaminoglycan composition described herein comprises hyaluronan and N-acetyl D-glucosamine, and optionally chondroitin sulfate. In yet another embodiment, the glycosaminoglycan composition described herein is a POLYGLYCAN® composition consisting essentially of chondroitin sulfate, N-acetyl D-glucosamine, and hyaluronan, wherein by combining the three components described herein, particularly in combination with a cellular therapy, the composition provides a synergistic effect in the treating connective tissue damage and repairing defective cartilage. Glycosaminoglycan compositions such as described in U.S. Pat. Nos. 6,979,679 and 7,485,629 are hereby incorporated by reference in their entireties.

It is believed that chondroitin sulfate acts to stimulate the production of proteoglycans, glycosaminoglycans, and collagen, inhibits degenerative enzymes excreted by the chondrocytes, and synoviocytes, and aids in nutrient transportation within the synovial fluid. It is believed that glucosamine derivatives, particularly N-acetyl D-glucosamine, increase the synoviocyte and chondrocyte production and subsequent availability of endogenous hyaluronan by the direct in situ inclusion of its prime substrates galactosamine (through chondroitin sulfate assimilation) and N-acetyl D-glucosamine. It is further believed that the exogenous hyaluronan acts to replace depleted endogenous HA and to lubricate and coat healthy as well as damaged articular tissue during the reparative process. The examples and proposed mechanisms of action set forth herein are in no way intended to limit the scope of the invention. Those of skill in the art will realize that, given the teachings provided herein, many variations of the compositions, methods of use thereof, are possible that will fall within the scope of the invention.

The glycosaminoglycan composition described herein provides a unique mixture comprised of the isolated naturally occurring agents: chondroitin 4-sulfate (CS4) and chondroitin 6-sulfate (CS6), hyaluronan and a suitable glucosamine derivative, e.g., N-acetyl D-glucosamine. It can be appreciated that, depending upon the target connective tissue, the suitable glucosamine derivative can be selected from any of the glucosamine derivatives including, but not limited to, glucosamine 5-phosphate, glucosamine sulfate sodium, glucosamine hydrochloride, N-acetyl D-glucosamine, and mixtures thereof. Synthetic derivatives of any of the identified naturally occurring agents can also be used in the invention.

Chondroitin sulfates are one of the important components of the glycosaminoglycan composition described herein. In general, chondroitin sulfates are widely found in the connective tissues of animals in two forms of repeating disaccharides of D-glucoronic acid and N-acetyl galactosamine: CS4 sulfate where n-acetyl galactosamine holds an ester sulfate in its CS4 position or CS6 sulfate where the ester sulfate is in the CS6 position. Both CS4 and CS6 chondroitin sulfate function in the articular matrix as a major constituent. Chondroitin sulfates contribute to keep the cartilage matrix's normal characteristics through the increase of the glucosaminoglycan pool used by the chondrocytes for proteoglycan synthesis, as well as slowing down the inflammatory process acting directly on the enzymes inhibiting the compliment cascade and by exhibiting anti-prostoglandin activity.

Another important component in the glycosaminoglycan composition described herein is hyaluronan and its salts (e.g., sodium hyaluronate). Hyaluronan is a natural constituent of connective tissues and synovial fluid composed of repeating disaccharide units each consisting of D-glucoranic acid and N-acetyl D-glucosamine. Within the joint capsule, the surface of articular cartilage is covered by a thin layer of sodium hyaluronate. It specifically interacts with cartilage proteoglycans to form a stabile aggregate. Within the synovial fluid it confers viscal elasticity as well as lubricating properties. Hyaluronan aids in providing nourishment and waste removal from the articular matrix. It also provides biochemical activity to help prevent excess fibrous tissue from forming in the cartilage matrix.

In addition, N-acetyl D-glucosamine is also one of the important components in the glycosaminoglycan composition described herein. The N-acetyl D-glucosamine is a key compound for cartilage matrix synthesis as it enhances chondrocyte synthesis of glucosaminoglycans. N-acetyl D-glucosamine also possesses the ability to enhance synthesis of key components of synovial fluid by feeding both reactions necessary for the production of hyaluronan as well as for proteoglycans. Therefore, by replacing specific glucosaminoglycans lost by the invasion of the diarthrodial joint during surgery and also providing the key molecules to enhance and promote the restoration of normal hyaluronan and proteoglycan synthesis, the physician or veterinarian can be assured of the composition's capability to protect the joint as well as to aid in the healing process.

As used herein, the chondroitin sulfate in the glycosaminoglycan composition can be CS4, CS6, or a mixture of both CS4 and CS6. The therapeutically effective amount of chondroitin sulfate and N-acetyl D-glucosamine can be from between about 0.5 grams to about 1.5 grams of per unit dose, respectively, and the therapeutically effective amount of hyaluronan can be from about 10 mg to about 50 mg per unit dose. In one embodiment, the therapeutically effective amount comprises about 1 gram of CS4 chondroitin sulfate, or about 1 gram of CS6 chondroitin sulfate or about 1 gram of a mixture of CS4 and CS6 chondroitin sulfate per unit dose. In another embodiment, the therapeutically effective amount of chondroitin sulfate is about 1 gram of chondroitin sulfate comprised of about 40% CS4 chondroitin sulfate and about 60% CS6 chondroitin sulfate.

A therapeutic amount of N-acetyl D-glucosamine can be about 1 gram of N-acetyl D-glucosamine per unit dose of the composition. Therapeutic amounts of hyaluronan include from about 10 mg to about 50 mg of hyaluronan per unit dose of the composition. Therapeutic amounts of hyaluronan can be from about 20 to about 40 mg of hyaluronan per unit dose of the composition.

It can be appreciated by one of skill in the art that the hyaluronan can be selected from among any of a number of commercially available sources, such as commercially available sodium hyaluronate, and can include alternative salts and metabolic precursors or metabolites thereof. Likewise there are numerous commercially available sources of N-acetyl D-glucosamine and chondroitin sulfate and various alternative salts or metabolic precursors or metabolites thereof that are available for use in the glycosaminoglycan composition described herein.

Another embodiment of the glycosaminoglycan composition provided herein comprises a sterile solution or suspension comprising about 1 gram of chondroitin sulfate as a mixture of about 40% CS4 and 60% CS6 chondroitin sulfate; about 1 gram of N-acetyl D-glucosamine; and about 20-40 mg but especially about 30 mg of hyaluronan (e.g., sodium hyaluronate) per unit dose of the glycosaminoglycan composition described herein.

One example of a glycosaminoglycan composition provided herein comprises a 10 ml unit dose, and is made as follows: one gram of chondroitin sulfate powder is admixed with one gram of N-acetyl D-glucosamine powder. These powders are weighed, admixed and 2 ml of a 10 mg/ml solution of sodium hyaluronate is added to the powder mixture. The resultant mixture of chondroitin sulfate, N-acetyl D-glucosamine and sodium hyaluronate can be qs with approximately 10 ml of bacteriostatic water to achieve a final volume of 10 ml. The final concentration of chondroitin sulfate in the glycosaminoglycan composition described herein can be 0.1 gram/ml or 10%. The final concentration of N-acetyl D-glucosamine in the glycosaminoglycan composition described herein can be 0.1 gram/ml or 10%, and the final concentration of sodium hyaluronate in the glycosaminoglycan composition described herein can be 0.2 ml/ml or 20%.

One embodiment of the glycosaminoglycan composition provided herein is, for example, POLYGLYCAN® that consists essentially of therapeutic amounts of chondroitin sulfate, N-acetyl D-glucosamine, and hyaluronan. The glycosaminoglycan composition described herein may specifically exclude other therapeutic agents, such as analgesics, or may specifically include other therapeutic agents, such as immunosuppressants or bactericides. The glycosaminoglycan composition described herein may specifically exclude chondroitin sulfate, and comprise or consist essentially of N-acetyl D-glucosamine and hyaluronan.

In one embodiment, the glycosaminoglycan composition provided herein comprises therapeutically effective amounts of chondroitin sulfate, N-acetyl D-glucosamine, and hyaluronan, wherein the molecular weight per each supramolecule per unit dose of the glycosaminoglycan composition described herein is from between about 450,000 Daltons to about 1,600,000 Daltons, preferably is from between about 500,000 Daltons to about 1,400,000 Daltons, more preferably is from between about 550,000 Daltons to about 700,000 Daltons, and most preferably is about 600,000 Daltons. In yet another embodiment, the glycosaminoglycan composition provided herein comprises therapeutic amounts of chondroitin sulfate, N-acetyl D-glucosamine, and hyaluronan, wherein the molecular weight per each supramolecule per unit dose of the glycosaminoglycan composition described herein is greater than about 450,000 Daltons, preferably is greater than about 550,000 Daltons.

Preparation of the glycosaminoglycan composition provided herein may be made by conventional methods. For example, to prepare the glycosaminoglycan composition of the invention, the above-described ingredients are combined as the active ingredient in intimate admixture with or without a suitable carrier according to conventional compounding techniques. This carrier may take a wide variety of forms depending upon the form of preparation desired for administration, e.g., oral, sublingual, nasal, guttural, rectal, transdermal, or parenteral.

The Stem Cell Preparation

The term "stem cell" as used herein refers to either (1) a multipotent, or lineage-uncommitted progenitor cell, which is isolated from embryonic, fetal or adult tissues, such as adipose, bone marrow, blood, dermis and periosteum, that are naturally or induced to be capable of differentiating into multiple specific types of mesenchymal or connective tissues (i.e., the tissues of the body that support the specialized elements; particularly adipose, osseous, cartilaginous, elastic, and fibrous connective tissues) depending upon various influences from bioactive factors, such as cytokines, or (2) a lineage-committed progenitor cell produced from the mitotic division of a stem cell which will eventually differentiate into a chondrocyte. Unlike the stem cell from which it is derived, the lineage-committed progenitor is generally considered to be incapable of an unlimited number of mitotic divisions and will eventually differentiate into a chondrocyte. Therefore, a "stem cell" as used herein is selected from any number of non-terminally differentiated cells.

Methods for isolating, purifying, and replicating these stem cells in culture, i.e. in vitro, for the stem cell preparations provided herein are provided based on the conventional methods known in the art. For example, U.S. Pat. Nos. 5,197,985; 5,486,359; 5,226,914 to Caplan et al. (the entire contents of which are incorporated herein by reference) relate to culturing marrow-derived mesenchymal stem cells in vitro in the presence of growth factors, applying these cells to a carrier to promote cell morphology, and implanting the carrier containing the cells into damaged articular cartilage. U.S. Pat. No. 6,936,281 to Seshi (the entire contents of which is incorporated herein by reference) provides methods for isolating and purifying human mesenchymal progenitor cells (MPCs) from Dexter-type cultures, and their therapeutic uses for diagnostic purposes, and to enhance the negraftment of hematopoietic progenitor cells, enhance bone marrow transplantation, or aid in the treatment or prevention of graft versus host disease.

A stem cell, or chondrocyte progenitor cell, of the invention can also be isolated from other tissue sources including adipose, such as falciform tissue. Several exemplary commercially available systems exist for the isolation of such stem cells from adipose, including those from InGeneron, Inc. (Houston, Tex.), MediVet America Inc., (Nicholasville, Ky.) and Vet-Stem, Inc. (Poway, Calif.). For example, stem cells of the present invention can be prepared using the Autologous Regenerative Cell System (ARC System) provided by InGeneron, Inc., which is described in detail in the U.S. Patent Application Publication No. 2010/0285588 (the entire contents of which are incorporated herein by reference). The ARC system is designed for rapid point-of-care preparation of regenerative cells from adipose tissue in settings where small quantities of tissue are available, such as applications in veterinary medicine. The ARC system comprises an apparatus for isolating cells from adipose tissue that includes a lipid separating apparatus having one or more dispersing ports equipped with a plurality of pores (or other means of dispersion) and a cell separation assembly that includes a plurality of optionally removable filters of variable pore size. The cell separation assembly is arranged to interface with a lipoaspiration device and to selectively separate and elute cells.

The ARC System comprises a unitary disposable apparatus and its associated components and instructions packaged in a kit, used for rapidly isolating and/or recovering stromal vascular fraction (SVF) cells and/or a reparative cell population comprising viable non-adipocyte cells (e.g., preadipocytes, mesenchymal stromal cells, endothelial cells, endothelial progenitor cells, fibroblasts, macrophages and lymphocytes) from adipose tissue. The apparatus includes a container/digestion chamber adapted for processing adipose tissue into individual cells and small clusters of cells to a diameter of about 1000 microns or less and a lipid separating unit adapted to separate the processed adipose tissue without the need for centrifugation into a lipid layer enriched in adipocytes and an aqueous layer enriched in stromal vascular fraction cells. Stromal cells isolated from adipose tissue can yield cell preparations useful for the repair of articular cartilage. Additionally, these stromal cells can be cultured to differentiate into cells having neuronal characteristics. Likewise, adipose-derived stromal cells can be used as a source in generating hematopoietic cells, osteogenic cells, endothelial cells, adipocytes and myocytes of skeletal and smooth muscle.

More specifically, the unitary disposable apparatus provided for recovering cells from a biological tissue without a need for centrifugation includes a digestion chamber adapted to receive and dissociate the biological tissue into a digestion mixture including cells and cell clusters and a lipid separating unit in fluid communication with the digestion chamber and adapted for phase separation of the digestion mixture into an aqueous cellular layer and a lipid layer that includes free lipids and cells that contain lipid droplets such as adipocytes. The aqueous cellular layer refers to a layer of cells that lack internal lipid droplets as are found in adipocytes. The digestion chamber of the apparatus is divided by an internal digestion mesh into post-digestion chamber and a predigestion chamber. The digestion chamber and associated fluid conduits are adapted to provide a recirculating fluid path through the pre-digestion and post-digestion chambers via a recirculating tubing circuit. Typically, a motive force for a fluid flow through the apparatus is provided by one or more pumps.

A heat exchanger is disposed in functional communication with the recirculating tubing circuit and the fluid flow is directed through the heat exchanger by the motive force of the one or more pumps. The heat exchanger is able to adapt the temperature of fluid flowing through the digestion chamber and thereby control activity of digestion enzymes utilized to digest the connective tissues that hold the tissue together. The one or more pumps and the heating exchanger are external to the apparatus and the apparatus is a one-time use disposable unit.

The internal digestion mesh is fixed in a vertical cylindrical orientation within the digestion chamber such that the pre-digestion chamber and the post-digestion chamber are in a concentric orientation. In one configuration, the outer concentric chamber is the predigestion chamber and the inner chamber is the post digestion chamber. In this configuration, a maximum surface area and exposure to fluid flow is provided to the pre-digested tissue and clogging of the digestion mesh is minimized. At least one dispersing filter is disposed in the fluid communication between the digestion chamber and the lipid separating unit. The dispersing filter can also be disposed in a fixed horizontal plane and is arranged in a perpendicular orientation to the digestion mesh.

In one aspect, the apparatus is a unitary combination of digestion chamber, dispersing filter and lipid separating unit in a single sterilizable and disposable unit that forms closed flow path from the initial introduction of tissue into the unit until isolated individual cells and small clusters of cells are removed from the unit. In such apparatus, the bottom of the digestion chamber forms a top of the lipid separating unit and the dispersing filter is disposed circumferentially, and integrated near a top aspect, of the lipid separating unit such that the surface area of the dispersing filter is maximized and the size of the lipid separating unit is minimized.

The digestion chamber of the apparatus can also be divided by an internal digestion mesh into a post-digestion chamber and a concentric pre-digestion chamber. In this configuration, the digestion chamber as a whole includes at least one inlet port configured to introduce adipose containing tissue into the pre-digestion chamber and at least one outlet port configured to recover a digested cell mixture out of the post-digestion chamber and a fluid conduit connecting the pre-digestion chamber and the post-digestion chamber and adapted to provide a recirculating fluid flow from the post-digestion chamber and back to the pre-digestion chamber. The post digestion chamber is in fluid communication with a lipid separating unit and the lipid separating unit has at least one dispersing port equipped with a plurality of dispersing pores through which the digested cell mixture enters the lipid separating unit. The pores of the dispersing port effect further disruption of cell clusters as they enter the lipid separating unit such that desired non-lipid containing cells are generally dissociated from the adipocytes. The dispersing port is located proximal to the bottom of the lipid separating unit and the pores are directed downward such that the flow path of the cell mixture out of the dispersing head maximizes fluid shear applied to the cells.

The lipid separating unit is adapted for phase separation of lipids and lipid containing cells from a population of non-lipid containing cells and includes a collection port disposed in the lipid separating unit to collect the population of non-lipid containing cells from under the floating lipid layer. When disposed in a unitary sterilizable apparatus having closed flow path, collection of various cells from adipose containing tissue is provided without a need for centrifugation. In one aspect, at least one filter is disposed in the fluid flow path between the digestion chamber and the lipid separating unit. In one aspect, apparatus includes a digestion mesh having a pore size of about 1,000 microns, at least one dispersing filter having a pore size of about 250 microns and dispersing head having pores with a pore size of about 500 microns.

The method of preparing a population of cells for cell transplantation can include the following steps: a) dissociating a sample of donor adipose tissue into individual cells and small clusters of cells until the dissociated cells and clusters of cells are reduced in diameter to about 1,000 microns or less, such as about 500 microns or less, or even about 250 microns or less; b) phase separating the individual cells and small clusters of cells into an aqueous cellular layer and a lipid layer without centrifugation; and c) collecting cells (e.g., stromal vascular fraction cells or a reparative cell population of stem cells) for cell transplantation from the aqueous cellular layer.

More specifically, the method provided herewith for separating stem cells from tissue includes the steps of introducing a tissue into a digestion chamber that includes a digestion fluid and an internal digestion mesh, recirculating the digestion fluid across the digestion mesh until the tissue is separated into a digestion mixture that includes individual cells and cell clusters, followed by phase separating the digestion mixture through an aqueous medium disposed in a lipid separating unit. After the phase separation, wherein the constituent cells of the digestion mixture are separated on the basis of density in an aqueous medium, desired stem cell populations are collected from below the floating lipids and lipid containing cells within the separating unit.

The stem cell preparations provided herein can provide a direct source of stromal cells, e.g., chondrocytes and/or chondrocyte progenitor cells, that are capable of migrating to the defected site, attaching thereto, and elaborating cartilage-specific macromolecules and extracellular matrix proteins for the production of new cartilage at the defect site. The stem cell preparation provided herein may also provide cells that produce biological factors that promote chondrogenesis and the migration of cells such as chondrogenic stem cells or chondrocytes, from the in vivo environment, including from the periosteal/perichondrial tissue, adjacent to the defect site, and/or differentiation thereon and therein.

The stem cell preparation provided herein may include chondrocytes, chondrocyte progenitor cells including mesenchymal stem cells, fibroblasts, fibroblast-like cells and/or cells capable of producing collagen type II and other collagen types, and proteoglycans which are typically produced in cartilaginous tissues. The stem cells can be obtained from the patient (or subject) or a histocompatible donor. The chondrocytes, progenitor cells, fibroblast-like cells and other cells and/or elements that comprise the stroma may be fetal or adult in origin, and may be derived from convenient sources such as cartilage, bone, skin, ligaments, tendons, muscles, placenta, umbilical cord, etc. For example, stromal cells such as chondrocytes may be derived from any type of cartilage, including but not limited to, hyaline cartilage, costal cartilage, fibrous cartilage, etc., which can be obtained by biopsy (where appropriate) or upon autopsy. Chondrocyte progenitor cells may be derived from various sources including bone marrow, periosteum, perichondrium or various sources of undifferentiated human mesenchyme. Fibroblasts can be obtained in quantity rather conveniently from foreskin, preferably fetal foreskin, or, alternatively, any appropriate cadaver organ. Fetal cells, including fibroblast-like cells and chondrocyte progenitor cells, may be obtained from umbilical cord or placenta tissue or umbilical cord blood. Although stem cells from a variety of sources may be used in the prevent invention, the stem cells can be derived from cells of fetal origin which may be viewed as "universal donors" so as to minimize the risk of immunological rejection. Alternatively, obtaining stem cells from mature adult sources is also very useful, particularly for autologous transplantation.

The stromal cells may be readily isolated by disaggregating an appropriate tissue which is to serve as the source of the cells. This may be readily accomplished using techniques known to those skilled in the art. For example, the tissue can be disaggregated mechanically and/or treated with digestive enzymes and/or chelating agents that weaken the connections between neighboring cells making it possible to disperse the tissue into a suspension of individual cells without appreciable cell breakage. Enzymatic dissociation can be accomplished by mincing the tissue and treating the minced tissue with any of a number of digestive enzymes either alone or in combination. These include but are not limited to trypsin, chymotrypsin, collagenase, elastase, and/or hyaluronidase, Dnase, pronase, etc. Mechanical disruption can also be accomplished by a number of methods including, but not limited to the use of grinders, blenders, sieves, homogenizers, pressure cells, or sonicators to name but a few. For a review of tissue disaggregation techniques, see Freshney, Culture of Animal Cells. A Manual of Basic Technique, latest edition, A. R. Liss, Inc., New York, 1987, Ch. 9.

Once the tissue has been reduced to a suspension of individual cells, the suspension can be fractionated into subpopulations from which chondrocytes, fibroblasts and/or other stromal cells and/or elements can be obtained. This also may be accomplished using standard techniques for cell separation including but not limited to cloning and selection of specific cell types, selective destruction of unwanted cells (negative selection), separation based upon differential cell agglutinability in the mixed population, freeze-thaw procedures, differential adherence properties of the cells in the mixed population, filtration, conventional and zonal centrifugation, centrifugal elutriation (counter-streaming centrifugation), unit gravity separation, counter current distribution, electrophoresis and fluorescence-activated cell sorting. For a review of clonal selection and cell separation techniques, see Freshney, supra, Ch. 11 and 12.

For example, the isolation of chondrocytes, chondrocyte progenitors, fibroblasts or fibroblast-like cells is carried out as follows: fresh human cartilage tissue can be thoroughly washed and minced in Hanks balanced salt solution (HBSS) in order to remove serum. The minced tissue is incubated from 1-12 hours in a freshly prepared solution of a dissociating enzyme such as trypsin. After such incubation, the dissociated cells are suspended, pelleted by centrifugation and plated onto culture dishes. All fibroblasts will attach before other cells, therefore, appropriate stromal cells can be selectively isolated and grown. The isolated stromal cells can then be grown to confluency, lifted from the confluent culture and administered to the cartilage defect site in vivo (see, e.g., Naughton et al., 1987, J. Med. 18(3&4):219-250). Fibroblast-like cells may also be isolated from human umbilical cords (33-44 weeks). Fresh tissues may be minced into pieces and washed with medium or snap-frozen in liquid nitrogen until further use. The umbilical tissues may be disaggregated as described above.

Once chondrocytes or chondrocyte progenitor cells have been isolated, their population can be expanded mitotically in vitro in order to obtain the cell preparation for administration. Methods for the selection of the most appropriate culture medium, medium preparation, and cell culture techniques are well known in the art and are described in a variety of sources, including Doyle et al., (eds.), 1995, Cell & Tissue Culture: Laboratory Procedures, John Wiley & Sons, Chichester; and Ho and Wang (eds.), 1991, Animal Cell Bioreactors, Butterworth-Heinemann, Boston.

The cells can be transferred or "passaged" to fresh medium when they reach an appropriate density, such as 3 to $6.5 \times 10^4/\text{cm}^2$, or, for example, when they reach a defined percentage of confluency on the surface of a culture dish. During incubation, the stromal cells may stick to the walls of the culture vessel where they can continue to proliferate and form a confluent monolayer. This can be prevented or minimized, for example, by transferring a portion of the cells to a new culture vessel having fresh medium, since the presence of a confluent monolayer in the culture vessel will tend to "shut down" the growth of cells in the culture. Removal of the confluent monolayer or transfer of a portion of the cells to fresh media in a new vessel will usually restore proliferative activity of the cells. Such removal or transfer should be done in any culture vessel which has a monolayer exceeding about 25% confluency. Alternatively, the liquid culture can be agitated, for example, on an orbital shaker or in roller bottles, to prevent or minimize the cells from sticking to the vessel walls.

In addition, once the stromal cells have been established in culture, they may be maintained or stored in cell "banks" comprising either continuous in vitro cultures of cells requiring regular transfer, or cells which have been cryopreserved. Cryopreservation of the cells may be carried out according to known methods, such as those described in Doyle et al., 1995, supra. Cryoprotective agent and its use in cryopreservation of cellular matter is disclosed in U.S. Pat. No. 5,071,741 to Brockbank (the entire contents of which is incorporated herein by reference). Furthermore, compositions and methods for culturing and freezing cells and tissues are also disclosed in U.S. Pat. No. 5,102,783 to Alkemade et al. (the entire contents of which is incorporated herein by reference).

For example, but not by way of limitation, cells may be suspended in a "freeze medium" such as, for example, culture medium further comprising 20% FBS and 9% dimethylsulfoxide (DMSO), with or without 5-10% glycerol, at a density, for example, of about $4\text{-}10 \times 10^6$ cells/ml. The cells are dispensed into glass or plastic ampoules (Nunc) which are then sealed and transferred to the freezing chamber of a programmable freezer. The optimal rate of freezing may be determined empirically. For example, a freezing program that gives a change in temperature of −1° C./min through the heat of fusion may be used. Once the ampoules have reached −180° C., they are transferred to a liquid nitrogen storage area. Cryopreserved cells can be stored for a period of years, though they should be checked at least every 5 years for maintenance of viability.

The cryopreserved cells constitute a bank of cells, portions of which can be "withdrawn" by thawing and then used to produce new cartilage tissue as needed. Thawing should generally be carried out rapidly, for example, by transferring an ampoule from liquid nitrogen to a 37° C. water bath. The thawed contents of the ampoule should be immediately transferred under sterile conditions to a culture vessel containing an appropriate medium such as RPMI 1640 conditioned with 10% FBS and 5% ES. It is advisable that the cells in the culture medium be adjusted to an initial density of about $3\text{-}6\times10^5$ cells/ml so that the cells can condition the medium as soon as possible, thereby preventing a protracted lag phase. Once in culture, the cells may be examined daily, for example, with an inverted microscope to detect cell proliferation, and subcultured as soon as they reach an appropriate density.

In addition to chondrocytes, chondrocyte progenitors, fibroblasts or fibroblast-like cells, other cells which aid in the production of desired cells may be added to the stem cell preparation for administration. For example, other cells found in loose connective tissue may be seeded along with chondrocytes or fibroblasts. Such cells include but are not limited to endothelial cells, pericytes, macrophages, monocytes, plasma cells, mast cells, adipocytes, etc. These stromal cells may readily be derived from appropriate organs including umbilical cord or placenta or umbilical cord blood using methods known in the art such as those discussed above.

Moreover, the stem cell preparation may further comprise one or more other components, including selected extracellular matrix components, such as one or more types of collagen known in the art, as well as growth factors and/or drugs. Growth factors which may be usefully incorporated into the stem cell preparation include one or more tissue growth or stimulatory factors known in the art or to be identified in the future, including but not limited to any member of the TGF-β family, BMPs that stimulate cartilage formation, e.g., BMP-2, BMP-12, and BMP-13, factors that stimulate migration of stromal cells and/or matrix deposition, insulin-like growth factor (IGF)-I and -II, fibroblast growth factor (FGF), Actavin, growth hormone, etc.

Drugs which may be usefully incorporated into the stem cell preparation include anti-inflammatory compounds such as non-steroidal anti-inflammatories, immunosuppressants such as the cyclosporins, as well as local anesthetics. Other components may also be included in the stem cell preparation, including but not limited to any of the following: (1) buffers to provide appropriate pH and isotonicity; (2) lubricants; (3) viscous materials to retain the cells at or near the site of administration, including, for example, alginates, agars and plant gums; and (4) other cell types that may produce a desired effect at the site of administration, such as, for example, enhancement or modification of the formation of cartilage tissue or its physicochemical characteristics, or support for the viability of the cells, or inhibition of inflammation or rejection.

According to one embodiment of the invention, growth regulatory or stimulatory factors including, but not limited to, TGF-β and ascorbate, or BMPs that stimulate cartilage formation such as BMP-2, BMP-12, and BMP-13 may be added to the administration site before, during or after administration of the stem cell preparation in order to promote the production of new cartilage at the site. Moreover, such growth regulatory factors can be administered to the site at the time of administration of the stromal cells, either as a separate preparation or, as noted supra, as part of the stromal cell preparation.

In addition, the stromal cells may be genetically engineered to produce growth factors such as TGF-β, as well as other biological factors such as factors that stimulate chondrogenesis or the migration of chondrogenic and other stromal cells to the defected site. The stromal cells as provided herein can be genetically engineered to produce gene products that promote the successful production or repair of cartilage at a defect site and/or for use in gene therapies. For example, the stromal cells can be genetically engineered to express anti-inflammatory factors, e.g., anti-GM-CSF, anti-TNF, anti-IL-1, anti-IL-2, etc., to reduce the risk of rejection or degenerative changes in the cartilage due to rheumatoid disease or other inflammatory reactions. Also, the stromal cells can be genetically engineered to express peptides or polypeptides corresponding to the idiotype of neutralizing antibodies for granulocyte-macrophage colony stimulating factor (GM-CSF), TNF, IL-1, IL-2, or other inflammatory cytokines. IL-1 has been shown to decrease the synthesis of proteoglycans and collagens type II, IX, and XI (Tyler et al., 1985, Biochem. J. 227:869-878; Tyler et al., 1988, Coll. Relat. Res. 82:393-405; Goldring et al., 1988, J. Clin. Invest. 82:2026-2037; and Lefebvre et al., 1990, Biophys. Acta. 1052:366-372) and is a potent stimulator of cartilage resorption and of the production of inflammatory mediators by chondrocytes (Campbell et al., 1991, J. Immunol. 147:1238-1246). TNF also inhibits synthesis of proteoglycans and type II collagen, although it is much less potent than IL-1 (Yaron, I., et al., 1989, Arthritis Rheum. 32:173-180; Ikebe, T., et al., 1988, J. Immunol. 140:827-831; and Saklatvala, J., 1986, Nature 322:547-549). Once the genetically engineered stromal cells are administered into an individual, the presence of the anti-inflammatory gene products can bring about amelioration of immunological rejection or the inflammatory reactions associated with rheumatoid or joint disease.

In another embodiment, the stromal cells can be genetically engineered to express a gene which would exert a therapeutic effect, e.g., in the production of TGF-β to stimulate cartilage production, or other factors such as BMP-13 to promote chondrogenesis and/or prevent bone formation or stimulatory factors that promote migration of stromal cells and/or matrix deposition. In addition, the stromal cells can be genetically engineered to express a gene for which a patent is deficient. For example, genes that prevent or ameliorate symptoms of various types of rheumatoid or joint diseases may be underexpressed or down-regulated under disease conditions. Specifically, expression of genes involved in preventing inflammatory reactions in rheumatoid or joint diseases may be down-regulated.

Alternatively, the activity of gene products may be diminished, leading to the manifestations of some or all of the above pathological conditions and eventual development of symptoms of rheumatoid or joint diseases. Thus, the level of gene activity may be increased by either increasing the level of gene product present or by increasing the level of the active gene product present at the defect site. By administering stromal cells genetically engineered to express the active target gene product into the defect site of a rheumatoid or joint disease patient who is deficient for that product, the level of the target gene product and/or the activity of that product can be modulated to prevent or ameliorate the symptoms of rheumatoid or joint diseases. "Target gene," as used herein, refers to a gene involved in rheumatoid or joint diseases in a manner by which modulation of the level of target gene expression or of target gene product activity may act to ameliorate symptoms of rheumatoid or joint diseases by preventing resorption of cartilage and production of inflammatory mediators by chondrocytes.

In addition, patients may be treated by gene replacement therapy by administering the stromal cells provided herein. Thus, replacement or repaired cartilage may be designed specifically to meet the requirements of an individual patient; for example, the stromal cells may be genetically engineered to regulate one or more genes; or the regulation of gene expression may be transient or long-term; or the gene activity may be non-inducible or inducible.

The stromal cells provided herein can also be genetically engineered to "knock out" expression of factors that promote inflammation or rejection at the administration site. Negative modulatory techniques for the reduction of target gene expression levels or target gene product activity levels are discussed below. "Negative modulation", as used herein, refers to a reduction in the level and/or activity of target gene product relative to the level and/or activity of the target gene product in the absence of the modulatory treatment. The expression of a gene native to stromal cell can be reduced or knocked out using a number of techniques, for example, expression may be inhibited by inactivating the gene completely (commonly termed "knockout") using standard homologous recombination techniques. Usually, an exon encoding an important region of the protein (or an exon 5' to that region) is interrupted by a positive selectable marker (for example neo), preventing the production of normal mRNA from the target gene and resulting in inactivation of the gene. A gene may also be inactivated by creating a deletion in part of a gene, or by deleting the entire gene. By using a construct with two regions of homology to the target gene that are far apart in the genome, the sequences intervening the two regions can be deleted. Mombaerts et al., 1991, Proc. Nat. Acad. Sci. U.S.A. 88:3084-3087.

Antisense and ribozyme molecules which inhibit expression of the target gene can also be used to reduce the level of target gene activity. For example, antisense RNA molecules which inhibit the expression of major histocompatibility gene complexes (HLA) have been shown to be most versatile with respect to immune responses. Furthermore, appropriate ribozyme molecules can be designed as described, e.g., by Haseloff et al., 1988, Nature 334:585-591; Zaug et al., 1984, Science 224:574-578; and Zaug and Cech, 1986, Science 231:470-475. Still further, triple helix molecules can be utilized in reducing the level of target gene activity. These techniques are described in detail by L. G. Davis et al., eds, Basic Methods in Molecular Biology, 2nd ed., Appleton & Lange, Norwalk, Conn. 1994.

Using any of the foregoing techniques, the expression of IL-1 can be knocked out in the chondrocytes to reduce the risk of resorption of cartilage and production of inflammatory mediators by the chondrocytes. Likewise, the expression of MHC class II molecules can be knocked out in order to reduce the risk of rejection of the implant.

Methods that may be useful to genetically engineer the cells are well-known in the art. For example, a recombinant DNA construct or vector containing the gene of interest may be constructed and used to transform or transfect the stromal cells provided herein. Such transformed or transfected cells that carry the gene of interest, and that are capable of expressing said gene, are selected and clonally expanded in culture.

Methods for preparing DNA constructs containing the gene of interest, for transforming or transfecting cells, and for selecting cells carrying and expressing the gene of interest are well-known in the art. See, for example, the techniques described in Maniatis et al., 1989, Molecular Cloning, A Laboratory Manual, Cold Spring Harbor Laboratory Press, Cold Spring Harbor, N.Y.; Ausubel et al., 1989, Current Protocols in Molecular Biology, Greene Publishing Associates & Wiley Interscience, N.Y.; and Sambrook et al., 1989, Molecular Cloning: A Laboratory Manual, 2nd Ed., Cold Spring Harbor Laboratory Press, Cold Spring Harbor, N.Y.

The cells can be engineered using any of a variety of vectors including, but not limited to, integrating viral vectors, e.g., retrovirus vector or adeno-associated viral vectors; or non-integrating replicating vectors, e.g., papilloma virus vectors, SV40 vectors, adenoviral vectors; or replication-defective viral vectors. Where transient expression is desired, non-integrating vectors and replication defective vectors can also be used, since either inducible or constitutive promoters can be used in these systems to control expression of the gene of interest. Alternatively, integrating vectors can be used to obtain transient expression, provided the gene of interest is controlled by an inducible promoter. Other methods of introducing DNA into cells include the use of liposomes, lipofection, electroporation, a particle gun, or by direct DNA injection.

Hosts cells are preferably transformed or transfected with DNA controlled by, i.e., in operative association with, one or more appropriate expression control elements such as promoter or enhancer sequences, transcription terminators, polyadenylation sites, among others, and a selectable marker. Following the introduction of the foreign DNA, engineered cells may be allowed to grow in enriched media and then switched to selective media. The selectable marker in the foreign DNA confers resistance to the selection and allows cells to stably integrate the foreign DNA as, for example, on a plasmid, into their chromosomes and grow to form foci which, in turn, can be cloned and expanded into cell lines. This method can be advantageously used to engineer cell lines which express the gene product.

Any promoter may be used to drive the expression of the inserted gene. For example, viral promoters include, but are not limited to, the CMV promoter/enhancer, SV40, papilloma virus, Epstein-Barr virus, elastin gene promoter and β-globin. The control elements used to control expression of the gene of interest should allow for the regulated expression of the gene so that the product is synthesized only when needed in vivo. If transient expression is desired, constitutive promoters are used in a non-integrating and/or replication-defective vector. Alternatively, inducible promoters could be used to drive the expression of the inserted gene when necessary. Inducible promoters can be built into integrating and/or replicating vectors. For example, inducible promoters include, but are not limited to, metallothionien and heat shock protein.

A variety of methods may be used to obtain the constitutive or transient expression of gene products engineered into the stromal cells. The stromal cells can be engineered to express such gene products transiently and/or under inducible control during the post-operative recovery period, or as a chimeric fusion protein anchored to the stromal cells, for example, as a chimeric molecule composed of an intracellular and/or transmembrane domain of a receptor or receptor-like molecule, fused to the gene product as the extracellular domain. Once the stromal cells have been genetically engineered, they may be administered to the patient to produce new cartilage in cases of degenerative connective tissue disease or trauma.

Formulations and Administration

Both glycosaminoglycan composition and the stem cells provided herein can be formulated into any suitable pharmaceutically acceptable preparations and/or formulations for administration. For parenteral products, the carrier will usually comprise sterile water, although other ingredients may be included, e.g., to aid solubility or for preservation purposes. Injectable suspensions may also be prepared, in which case appropriate liquid carriers, suspending agents, and the like may be employed.

In alternative embodiments, the glycosaminoglycan composition described herein can be in sterile solution, suspension, or other pharmaceutically acceptable formulations. The glycosaminoglycan composition described herein can be applied directly to the affected connective tissue, or is adapted for intra-articular and/or systemic or parenteral administration. Systemic administrations can include, but are not limited to, intramuscular, intravenous or subcutaneous injection. Thus, in one embodiment, the glycosaminoglycan composition described herein which has been specially adapted for intra-articular use and/or parenteral (e.g., intravenous or intramuscular) are sterile solutions or suspensions comprised of therapeutic amounts of chondroitin sulfate, N-acetyl D-glucosamine, and hyaluronan. In addition to the aforementioned active agents, it can be appreciated by one of skill in the art that the glycosaminoglycan compositions described herein which are adapted for intra-articular use, and other therapeutic uses, can also comprise preservatives, pharmaceutically active carriers, excipients, stabilizers, buffers, antimicrobial growth inhibitors and the like, and the use of such is contemplated by the invention.

It is also contemplated that other formulations for the glycosaminoglycan composition provided herein are also possible and are within the scope of the invention, e.g., a powdered formulation suitable for reconstitution with a suitable injectable liquid or for addition to a pre-selected lavage fluid. In particular, it can be appreciated by one of skill in the art that the active agents of the glycosaminoglycan composition can be stored in a freeze dried or lyophilized state for reconstitution and use at a desired time.

In yet another embodiment, the glycosaminoglycan composition described herein is attached to an impregnated bolus or a sheet of material adapted for implantation directly onto or between connective tissues of a mammalian body, for example to prevent the formation of post-operative adhesions, e.g., scar tissue formation. The glycosaminoglycan composition described herein can be impregnated into an absorptive gauze-like material or coated onto the material or joined to the material by adhesion and/or capillary action to a mesh or gauze. The material onto which the glycosaminoglycan composition is attached or absorbed may be either a permanent implant or it may be biodegradable. In one embodiment, the therapeutic glycosaminoglycan composition can be dispersed on or within a malleable material which can be shaped for insertion into diseased or excised tissue spaces. In yet another embodiment, the glycosaminoglycan composition described herein can be attached to a bandage or other surgical materials, including but not limited to surgical suture material, surgical staple, or a device such as a buckle. Surgically implanted devices and sheet of materials having drugs/compositions attached thereon are disclosed in U.S. Pat. No. 6,534,693 (the entire contents of which is incorporated herein by reference).

The stem cell preparations provided herein can be administered either before, during (as an admixture or generally concurrently), or after administration of the glycosaminoglycan composition. For example, the stem cells and/or the stem cell preparations can be seeded into the defect site before, during or after administration of the glycosaminoglycan composition, e.g., by injection into, and/or direct application to the defect site. When the stem cells are injected into the site, such injection can be achieved by any means that maintains the viability of the cells, e.g., via syringe or more preferably, via an arthroscope. According to an embodiment of the present invention, the number of stem cells administered can range from approximately $1 \times 10^6$ to $30 \times 10^6$ stem cells. In yet another embodiment, the stem cell preparations provided herein can also be mixed with the glycosaminoglycan composition provided herein immediately before the administration to the defect site.

According to an embodiment of the present invention, the stem cells to be seeded are surgically obtained from a subject, e.g., from adipose tissue, cartilage and/or bone marrow, in a separate surgical procedure, isolated, potentially cultured in vitro, to obtain an appropriate amount of cells and administered to the subject. The stem cells provided herein can form a stromal matrix that resembles the in vivo microenvironment of cartilage tissue, allowing for the production of new cartilage at the defect site. The stem cells administered to the site provide important biological factors that promote chondrogenesis and the migration of stromal cells, thus promoting the production of a living stromal tissue that provides the support, growth factors, and regulatory factors necessary to sustain long-term active proliferation of the stromal cells in vivo. The stem cells provided herein may additionally provide factors that promote the deposition of the living stromal matrix at the defect site. The proliferating cells mature and segregate properly within the matrix to form new cartilage tissue at the defect site in vivo.

The successful repair or replacement of damaged cartilage can be enhanced if the new cartilage tissue can be fixed in place at the site of repair. Post-implantation movement may cause the new cartilage tissue to become dislodged from the site if a pro-active fixation technique is not employed. Various methods can be used to fix the new cartilage tissue in place, including: patches derived from a bioresorbable polymer or biocompatible tissues, which can be placed over the site and sutured; bioabsorbable sutures or other fasteners, e.g., pins, staples, tacks, screws, anchors, glues, e.g., fibrin glue; non-absorbable fixation devices, e.g., sutures, pins, screws and anchors; adhesives; and the use of interference fit geometries.

Treatment and/or Repair of Connective Tissue Damage

It is contemplated by the present invention that the pharmaceutical preparations comprising the glycosaminoglycan composition and stem cells or the stem cell preparation described herein demonstrate enhanced effectiveness in the treatment of primary or secondary damage and injury to any connective tissues in humans and animals. Such diseases and injuries include, but are not limited to, arthritic diseases, osteoarthritis (OA), rheumatoid arthritis (RA), osteochondrosis dessicans (OCD), cartilage damage, joint injuries, joint inflammation, joint synovitis, degenerative joint disease (DJD), post surgical DJD, traumatic injuries, fractures, tendon damage, ligament damage, skeletal damage, musculoskeletal damage, bone damage, fiber damage, adipose tissue damage, blood cell damage, and plasma damage, and the like.

In one embodiment of the invention, a pharmaceutical preparation comprising a glycosaminoglycan composition in combination with stem cells or a stem cell preparation, and methods of using such pharmaceutical preparation described herein for the treatment of rheumatoid arthritis (RA) are provided. Rheumatoid arthritis is thought to be a human autoimmune disease characterized by chronic inflammation of the synovial joints and progressive erosion of the articular cartilage matrix. Although the etiology and pathology of rheumatoid arthritis is not totally understood, certain parameters are almost always present. Cytokines, free radicals, reactive oxygen species and degrading enzymes are formed as a result of phagocytic activity in the rheumatoid arthritis affected joint. Inflammatory mediators such as IL1, TNF, MMPs, RNOs have long been implicated as mediators of articular damage in rheumatoid arthritis as well as low molecular weight HA. The biological response to the presence of these products in rheumatoid arthritis joints may explain the increase in GAG levels present as the body's defense mechanisms become overwhelmed as the disease progresses.

While not wishing to be bound by any particular theories of activity, it is postulated herein that the body's normal response to rheumatoid arthritis may not be effective in controlling its pathology, and an endogenous increase of specific GAGs, as provided by the compositions of the invention, will result in a more favorable long term response to treatment of rheumatoid arthritis. The present invention provides that administration of a pharmaceutical preparation comprising a glycosaminoglycan composition comprising one or more GAGs, or homologs or anologs thereof, in combination with stem cells or a stem cell preparation, as set forth herein, will reduce the production and presence of the aforementioned inflammatory mediators via specific biological and chemical pathways, and promote the production of a living stromal tissue that provides the support, growth factors, and regulatory factors necessary to sustain long-term active proliferation of the stromal cells in vivo, thus, allowing production of new cartilage or other relevant connective tissues in the defect site.

Accordingly, the present invention provides methods of treatment for connective tissue conditions including rheumatoid arthritis comprising periodic administrations of therapeutic amounts of the pharmaceutical preparation comprising a glycosaminoglycan composition in combination with stem cells or a stem cell preparation, as described herein. It can be appreciated by one of skill in the art that the treatment regimen (e.g., frequency of administration and dosage) will vary according to the history, signalment, clinical stage and/or severity of the rheumatoid arthritis disease in a particular subject. In certain embodiments of the invention, the pharmaceutical preparation of the invention may be used in conjunction with other known rheumatoid arthritis treatment agents such as, e.g., DMARDs, TNF blockers, IL-1Ras, immunosuppressants and the like.

One method provided by the present invention is a first treatment regimen comprising a pretreatment with, e.g., a suitable DMARD, TNF blocker, or other immunosuppressant in conjunction with the pharmaceutical preparation comprising a glycosaminoglycan composition and stem cells or a stem cell preparation, or as a separate pre-treatment to provide a systemic short term down regulation of the disease process, followed by a second regimen of treatment with the pharmaceutical preparation comprising a glycosaminoglycan composition and stem cells or a stem cell preparation to normalize and stabilize the body's response to alleviate the symptoms of rheumatoid arthritis on a long term basis without the deleterious side effects of e.g., systemic immunosuppressant agents such as TNF blockers. It is contemplated that the initial treatment regimen with, e.g., a suitable DMARD, TNF blocker or other immunosuppressant can be in conjunction with therapeutic amounts of the pharmaceutical preparation comprising a glycosaminoglycan composition and stem cells or a stem cell preparation, as provided herein.

In yet another embodiment of the present invention the pharmaceutical preparation comprising a glycosaminoglycan composition and stem cells or a stem cell preparation, as set forth herein, can further comprise a therapeutically effective amount of other suitable therapeutics including, but not limited to, antibiotics. For instance, suitable antibiotics for use in the compositions provided herein include, but are not limited to any of the antibiotics that can be adapted for intra-articular use, (see, e.g., "Infectious Arthritis" Alicia L. Bertone, pp. 397-409, in Joint Disease in the Horse," W. B. Sanders, 1996 (ISBN 0-7216-5135-6)). As can be appreciated by one of skill in the art, the choice of antibiotics and other suitable therapeutics, and their therapeutically effective amounts, can depend many factors including, but not limited to, e.g., the etiology of the infectious organism being treated or personal preference of the treating veterinarian or physician.

The pharmaceutical preparation comprising a glycosaminoglycan composition and stem cells or a stem cell preparation, as provided herein, can also further comprise or exclude other therapeutic agents insofar as it is generally used as a therapeutic for connective tissue disease (e.g., tendonitis). Examples of other such therapeutic agents include, but are not limited to, synthetic and non-synthetic corticosteroid agents, nonsteroidal anti-inflammatory drugs, antirheumatics, immunoregulators, immunosuppressant, articular function augmenters, and interleukin production inhibitors. Specific examples of corticosteroid agents include, but are not limited to dexamethasone, hydrocortisone, triamcinolone, betamethasone, predonisolone, methylpredonisolone, halopredone, beclomethasone and the like. Specific examples of non-steroidal anti-inflammatory agents include, but are not limited to diclofenac, indomethacin, ibuprofen, ketoprofen, aspirin, diflunisal, fulfenamic acid, floctafenine, tolfenamic acid, sulindac, fenbufen, salicylic acid, acemetacin, proglumetacin, nabumetone, protizinic acid, thiaprofen, oxaprozin, loxoprofen, alminoprofen, zaltoprofen, flurbiprofen, flurbiprofen and the like.

In one embodiment, the pharmaceutical preparation comprising a glycosaminoglycan composition and stem cells or a stem cell preparation, as provided herein, can further comprise at least one pyrazolyl benzenesulfonamide compound, e.g., as set forth in U.S. Pat. No. 5,756,529 and U.S. Pat. No. 5,466,823 (the contents of which are incorporated herein by reference). In particular, the pharmaceutical preparation comprising a glycosaminoglycan composition and stem cells or a stem cell preparation, as provided herein, can further comprise a diaryl substituted pyrazole useful for treatment of inflammation and/or pain. It is specifically contemplated that the pharmaceutical preparation comprising a glycosaminoglycan composition and stem cells or a stem cell preparation, as provided herein, can further comprise therapeutic amounts of any of the class of diaryl substituted pyrazoles their isomers, analogs and/or metabolites. In particular, these compounds reduce inflammation and/or pain primarily via inhibition of cyclooxygenase-2 (COX-2). In an embodiment, the pharmaceutical preparation comprising a glycosaminoglycan composition and stem cells or a stem cell preparation, as provided herein, further comprises a non-steroidal agent that reduces inflammation and/or pain primarily via inhibition of cyclooxygenase-2 (COX-2) and with the substantial absence of inhibition of cyclooxygenase-1 (COX-1). Examples of suitable diaryl substituted pyrazoles for use in the pharmaceutical preparations of the present invention, include, but are not limited to, celecoxib, rofecoxib and the like.

Examples of other agents which may be added to the core pharmaceutical preparation comprising a glycosaminoglycan composition and stem cells or a stem cell preparation, as set forth herein, include axetil, piroxicam, tenoxicam, ampiroxicam, meloxicam, D-penicillamine, bucillamine, gold sodium thiomalate, auranofin, lobenzarit, salazosulfapyridine, methotrexate, cyclophosphamide, azathioprine, mizoribine, cyclosporin and the like.

In a particular embodiment, the present invention also provides a pharmaceutical preparation comprising a glycosaminoglycan composition and stem cells or a stem cell preparation, optionally with a suitable antioxidant or free radical scavenger. In one embodiment, the pharmaceutical preparation comprising a glycosaminoglycan composition and stem cells or a stem cell preparation, as provided herein, can further comprise a therapeutic amount of suitable superoxide dismutase (SOD) or other antioxidant including, but not limited to, examples set forth in U.S. Pat. No. 6,127,356 to Crapo et al., the contents of which are incorporated herein by reference.

The present invention further provides a method for treating connective tissue damage in humans or in animals comprising administering to a man or animal in need thereof, a therapeutically effective amount of the pharmaceutical preparation comprising a glycosaminoglycan composition and stem cells or a stem cell preparation, as provided herein. In one embodiment, the pharmaceutical preparation comprising a glycosaminoglycan composition and stem cells or a stem cell preparation, as described herein, is directly applied to the affected connective tissues. In another embodiment, the pharmaceutical preparation comprising a glycosaminoglycan composition and stem cells or a stem cell preparation, as provided herein, is adapted for intra-articular and/or systemic or parenteral administration. Systemic administrations can include, but are not limited to, intramuscular, intravenous or subcutaneous injection. The connective tissue damage referred herein include any primary or secondary diseases or injuries to the connective tissues in humans and/or animals Such diseases or injuries include, but are not limited to, arthritic diseases, osteoarthritis (OA), rheumatoid arthritis (RA), osteochondrosis dessicans (OCD), cartilage damage, joint injuries, joint inflammation, joint synovitis, degenerative joint disease (DJD), post surgical DJD, traumatic injuries, fractures, tendon damage, ligament damage, skeletal damage, musculoskeletal damage, bone damage, fiber damage, adipose tissue damage, blood cell damage, and plasma damage.

One skilled in the art will understand that, in a method for treating diseases of connective tissue, therapeutic dosage will vary according to the specific condition being treated and the severity of the disease, etc., and, therefore, can be given in a single dose, and then repeated as needed, or the dosage can be given incrementally in several smaller dosages. Thus, the pharmaceutical preparation of the present invention can be formulated such that the recommended therapeutic dose is achieved by the administration of a single dose or by the administration of several smaller doses. In certain methods, the injection is given systemically every 3-4 days to weeks, and the intralesional injection may be a single injection or a series of injections at, e.g., 3-week intervals.

Kit

It is apparent to one skilled in the art that the pharmaceutical preparation comprising a glycosaminoglycan composition and stem cells or components for producing a stem cell preparation, as provided herein, can be included in a commercial package together with instructions for its use against a disease of connective tissue. Thus, the present invention further provides a kit comprising one or more containers comprising the glycosaminoglycan composition, the stem cells or the components for isolating a stem cell preparation, and instructions for use of the glycosaminoglycan composition in combination of the stem cells or the stem cell preparations for treating connective tissue damages in man or in animals. The kit provided herein can also include other separate containers for other drugs, agents, compounds having desired therapeutic effects, including, but not limited to, synthetic and non-synthetic corticosteroid agents, nonsteroidal anti-inflammatory drugs, antirheumatics, immunoregulators, immunosuppressant, articular function augmenters, and interleukin production inhibitors.

The glycosaminoglycan composition, the stem cells or the stem cell preparations provided herein, each of which provided in the kit can be stored in any suitable container, including, but not limited to, syringes and vials, and in various dosage units. Preferably, the glycosaminoglycan composition comprises the dosages for chondroitin sulfate and N-acetyl D-glucosamine from between about 0.5 grams to about 1.5 grams per unit dose, respectively, and the dosage for hyaluronan from about 10 mg to about 50 mg per unit dose. Each component provided in the kit is formulated in sterile solutions, suspensions, or any pharmaceutically acceptable formulations, and stored in suitable containers, separately or in combination, in various dosage units. Preferably, the containers in the kit containing each of the component provided herein are disposable.

In one embodiment, the kit contains multiple preloaded syringes. At least one syringe is preloaded with a preselected volume of from between about 2 and about 10 ml of the glycosaminoglycan composition described herein in a sterile solution comprised of proportionate weight to volume ratios comprised of e.g., about 1 gram of chondroitin sulfate as a mixture of about 40% CS4 and 60% CS6 chondroitin sulfate, about 1 gram of N-acetyl D-glucosamine, and about 20-40 mg but especially about 30 mg of hyaluronan (e.g., sodium hyaluronate) per unit dose of the glycosaminoglycan composition. The preloaded syringe volume will of course vary depending upon the state of disease at the target tissue and species of animal, etc. The kit can also contain one or more separate syringes preloaded with a desired amount of other therapeutics well known in the art. In yet another embodiment, the kit contains at least three separate containers, one contains chondroitin sulfate, such as CS4 or CS6, or a mixture of 40% CS4 and 60% CS6, one contains N-acetyl D-glucosamine, and one contains hyaluronan (e.g., sodium hyaluronate). The three components are mixed in a desired dosage unit before it is administered.

In yet another embodiment, the kit provided herein contains a material adapted for implantation onto or between tissues of a mammalian body and with the pharmaceutical preparation comprising a glycosaminoglycan composition and stem cells or a stem cell preparation attached thereon. The material can be in the form of malleable semi-solid substrate, or a mesh or gauze-like carrier, and can be dissolvable or biodegradable. The pharmaceutical preparation comprising a glycosaminoglycan composition and stem cells or a stem cell preparation can be impregnated into the material or coated onto the material or joined to the material by adhesion and/or capillary action, such as to a mesh, gauze, or gauze-like material. Alternatively, the pharmaceutical preparation comprising a glycosaminoglycan composition and stem cells or a stem cell preparation is attached to the material that also includes, but is not limited to, a bandage, a surgical suture or staple material, and surgical device, such as buckle, suitable for a surgical process or device.

Furthermore, the kit provided herein includes instructions indicating a method of use of the pharmaceutical preparation comprising a glycosaminoglycan composition and stem cells or a stem cell preparation for treating any primary or secondary diseases or injuries to the connective tissues in humans or animals Such diseases or injuries include, but are not limited to, arthritic diseases, osteoarthritis (OA), rheumatoid arthritis (RA), osteochondrosis dessicans (OCD), cartilage damage, joint injuries, joint inflammation, joint synovitis, degenerative joint disease (DJD), post surgical DJD, traumatic injuries, fractures, tendon damage, ligament damage, skeletal damage, musculoskeletal damage, bone damage, fiber damage, adipose tissue damage, blood cell damage, and plasma damage. Instructions are normally in the form of a written material but are not limited to such.

Having discussed the pharmaceutical preparation comprising a glycosaminoglycan composition and stem cells or a stem cell preparation, as provided herein, and the method of use thereof, providing an enhanced effectiveness for the treatment of connective tissue damage, it will be more clearly perceived and better understood from the following specific examples which are intended to provide examples of certain embodiments and not limit the present invention.

EXAMPLES

Example 1

Adipose Tissue-Derived Stem Cell Preparation

Stem cells were prepared using the Autologous Regenerative Cell System (ARC System) (InGeneron, Inc., Houston, Tex.), which is described in detail above.

Example 2

Treatment with Glycosaminoglycan Composition in Combination with Stem Cell Therapy Case 1:
"Hobbs" Jones, a 13 year-old male canine, had multiple surgeries in the past to correct medial patella and secondary chondromalacia and osteoarthrosis/osteophytosis manifesting in progressive weight-bearing lameness on the left (L) side. Hobbs suffered from advanced degenerative joint disease on the left (L) stifle.
Stem Cell Preparation:
Falciform adipose tissue stem cells were harvested and prepared as described above in Example 1. Fat was obtained from a small abdominal incision at the umbilicus of the anesthetized animal. This falciform fat was utilized to obtain stem cells to inject into the knee.
Treatment Procedure:
1 ml of the stem cell preparation combined with 1 ml POLYGLYCAN® (hyaluronan, N-acetyl D-glucosamine and chondroitin sulfate) was injected intraarticularly at the left (L) stifle. SIMPLICEF® (200 mg) and TRAMADOL® (50 mg), were also administered one (1) tablet every 24 hours, and three (3) tablets every 12 hours, respectively. Hobbs was maintained on a normal diet, kept quiet with restricted household activities, and leashed outside only when necessary for 7-10 days. The incision site was monitored for increased swelling and any discharge or licking/chewing at site. Hobbs was rechecked on a follow-up visit every two weeks.
Treatment Results:
Definitive efficacy was obtained within one week after injection. No further improvements were observed, but sustained benefit remained for one month post injection.

Case 2:
"Shiloh" Helmey, a 9 year-old female German Shepherd, had previous bilateral tibial/fibular fractures four (4) years before the current treatment. She had recent plate removal and script infection on the right (R) tibia, and recent concurrent diagnosis of cranial cruciate ligament tear. Shiloh suffered from degenerative joint disease on the right (R) stifle.
Stem Cell Preparation:
Falciform adipose tissue harvested stem cells were harvested and prepared as described above in Example 1. Fat was obtained from a small abdominal incision at the umbilicus of the anesthetized animal. This falciform fat was utilized to obtain stem cells to inject into the knee.
Treatment Procedure:
1 ml of the stem cell composition combined with 1 ml POLYGLYCAN® was injected at the right (R) stifle. SIMPLICEF® (250 mg) and TRAMADOL® (50 mg), were also administered one (1) tablet every 24 hours, and four (4) tablets every 12 hours, respectively. Shiloh was on normal diet, but kept quiet with restricted household activities and leashed outside only when necessary for 7-10 days. The incision site was monitored for increased swelling and any discharge or licking/chewing at site. Shiloh was rechecked on a follow-up visit every week.
Treatment Results:
Definitive efficacy was obtained within 10 days after injection. Sustained benefit remained for one month post injection.
Case 3:
"Shitake" Harrelson, a 13 year-old male Great Dane, had previous tibial plateau leveling osteotomy on the right (R) side three (3) years before the current treatment. Shitake also had previous prepuce/penis amputation with scrotal uresthrostomy for neoplasia. He was recently diagnosed with progressive cranial cruciate ligament tear, as well as degenerative joint disease on the right (R) stifle.
Stem Cell Preparation:
Falciform adipose tissue harvested stem cells were prepared as described above in Example 1. Fat was obtained from a small abdominal incision at the umbilicus of the anesthetized animal. This falciform fat was utilized to obtain stem cells to inject into the knee.
Treatment Procedure:
1 ml of the stem cell composition combined with 1 ml POLYGLYCAN® was injected at the right (R) stifle. SIMPLICEF® (200 mg) and TRAMADOL® (50 mg), were also administered one (1) tablet every 24 hours, and six (6) tablets every 12 hours, respectively. Shitake was on normal diet, but kept quiet with restricted household activities and leashed outside only when necessary for 7-10 days. The incision site was monitored for increased swelling and any discharge or licking/chewing at site. Shiloh was rechecked on a follow-up visit every week.
Treatment Results:
Almost immediate benefits were noted, and sustained for three (3) weeks. Unfortunately, Shitake died due to complications from GI issues/aspiration pneumonia unrelated to the treatment.

The invention claimed is:
1. A composition comprising: a glycosaminoglycan composition comprising chondroitin sulfate, N-acetyl D-glucosamine, and hyaluronan; and stem cells, wherein the composition is provided in a container.
2. The composition of claim 1, wherein said chondroitin sulfate is a mixture of chondroitin 4-sulfate and chondroitin 6-sulfate.

3. The composition of claim 1, wherein said glycosaminoglycan composition consists essentially of chondroitin sulfate, N-acetyl D-glucosamine, and hyaluronan.

4. The composition of claim 1, adapted for parenteral administration.

5. The composition of claim 1, dispersed onto or within a semi-solid or solid material adapted for implantation onto damaged tissues.

6. The composition of claim 1, further comprising one or more therapeutic agents selected from the group consisting of a synthetic or a non-synthetic corticosteroid agent, nonsteroidal anti-inflammatory agent, antirheumatic agent, immunoregulation agent, immunosuppressant agent, articular function augmentor agent, growth factor, and interleukin production inhibitors.

7. The composition of claim 1, wherein said glycosaminoglycan composition comprises chondroitin sulfate in a concentration of about 50-100 mg/ml.

8. The composition of claim 7, wherein said glycosaminoglycan composition comprises chondroitin sulfate in a concentration of about 100 mg/ml.

9. The composition of claim 7, wherein chondroitin sulfate is chondroitin 4-sulfate, chondroitin 6-sulfate, or a mixture thereof.

10. The composition of claim 1, wherein said glycosaminoglycan composition comprises N-acetyl D-glucosamine in a concentration of about 50-100 mg/ml.

11. The composition of claim 10, wherein said glycosaminoglycan composition comprises N-acetyl D-glucosamine in a concentration of about 100 mg/ml.

12. The composition of claim 1, wherein said glycosaminoglycan composition comprises hyaluronan in a concentration of about 1-5 mg/ml.

13. The composition of claim 12, wherein said glycosaminoglycan composition comprises hyaluronan in a concentration of about 5 mg/ml.

* * * * *